US012693254B2

(12) United States Patent
Wen et al.

(10) Patent No.: US 12,693,254 B2
(45) Date of Patent: Jul. 28, 2026

(54) INTEGRATED REFERENCE ELECTRODE AND FLUID DISPENSER

(71) Applicant: Taiwan Semiconductor Manufacturing Co., Ltd., Hsinchu (TW)

(72) Inventors: Chin-Hua Wen, Toufen Township (TW); Jui-Cheng Huang, Hsinchu (TW)

(73) Assignee: Taiwan Semiconductor Manufacturing Co., Ltd., Hsinchu (TW)

( * ) Notice: Subject to any disclaimer, the term of this patent is extended or adjusted under 35 U.S.C. 154(b) by 1329 days.

(21) Appl. No.: 16/989,458

(22) Filed: Aug. 10, 2020

(65) Prior Publication Data

US 2020/0371059 A1    Nov. 26, 2020

Related U.S. Application Data

(63) Continuation of application No. 15/725,776, filed on Oct. 5, 2017, now Pat. No. 10,739,295.

(Continued)

(51) Int. Cl.
*G01N 27/30* (2006.01)
*B01L 3/00* (2006.01)
(Continued)

(52) U.S. Cl.
CPC .......... *G01N 27/301* (2013.01); *B01L 3/0262* (2013.01); *C12Q 1/6825* (2013.01); *G01N 27/414* (2013.01); *G01N 27/4145* (2013.01);

*G01N 33/5438* (2013.01); *B01L 3/502715* (2013.01); *B01L 2200/06* (2013.01); *B01L 2200/141* (2013.01); *B01L 2300/0645* (2013.01)

(58) Field of Classification Search
None
See application file for complete search history.

(56) References Cited

U.S. PATENT DOCUMENTS 2,925,370 A * 2/1960 Rohrer ................. G01N 27/401
65/61
3,463,717 A * 8/1969 Koopman ............ G01N 27/301
204/420

(Continued)

FOREIGN PATENT DOCUMENTS

CN        103299180 A      9/2013
TW        I453282 B        9/2014
(Continued)

*Primary Examiner* — James Lin
*Assistant Examiner* — Brittany I Fisher
(74) *Attorney, Agent, or Firm* — Sterne, Kessler, Goldstein & Fox P.L.L.C.

(57) ABSTRACT

An apparatus including an integrated reference electrode and a fluid dispenser is described. The reference electrode includes a body and a tip. The fluid dispenser at least partially surrounds the tip of the reference electrode and includes an inlet, a chamber, and an outlet. The fluid dispenser is configured to receive a fluid sample from the inlet to the chamber and form a droplet of the fluid sample through the outlet so that the droplet is in fluidic contact with the tip of the reference electrode and associated with a known potential determined by the reference electrode.

20 Claims, 15 Drawing Sheets

Related U.S. Application Data

(60) Provisional application No. 62/491,809, filed on Apr. 28, 2017.

(51) Int. Cl.
| | |
|---|---|
| *B01L 3/02* | (2006.01) |
| *C12Q 1/6825* | (2018.01) |
| *G01N 27/414* | (2006.01) |
| *G01N 33/543* | (2006.01) |

(56) References Cited

U.S. PATENT DOCUMENTS

| | | | |
|---|---|---|---|
| 4,273,637 A | | 6/1981 | MacDonald |
| 4,597,848 A | * | 7/1986 | Oka .................. G01N 27/3335 |
| | | | 204/418 |
| 4,891,125 A | | 1/1990 | Schultz |
| 8,227,258 B2 | | 7/2012 | Chang |
| 9,517,467 B1 | * | 12/2016 | Carrano ................. B01L 3/502 |
| 10,739,295 B2 | | 8/2020 | Wen et al. |

| | | | |
|---|---|---|---|
| 2002/0009392 A1 | * | 1/2002 | Wolk ................. G01N 35/1004 |
| | | | 204/453 |
| 2006/0257290 A1 | * | 11/2006 | Shimizu .................. B01L 3/502 |
| | | | 422/400 |
| 2007/0039866 A1 | | 2/2007 | Schroeder |
| 2010/0199788 A1 | | 8/2010 | Ayliffe |
| 2012/0067742 A1 | | 3/2012 | Lee et al. |
| 2012/0091008 A1 | * | 4/2012 | Muir .................. G01N 27/4167 |
| | | | 205/333 |
| 2012/0225435 A1 | | 9/2012 | Seger |
| 2013/0168250 A1 | | 7/2013 | Fogleman |
| 2013/0284597 A1 | | 10/2013 | Ren |
| 2013/0312546 A1 | | 11/2013 | Wada |
| 2016/0178594 A1 | | 6/2016 | Jarvis |
| 2016/0194697 A1 | | 7/2016 | Lee et al. |
| 2016/0238626 A1 | | 8/2016 | Bonzon |
| 2017/0038329 A1 | | 2/2017 | Yang |
| 2018/0313777 A1 | | 11/2018 | Wen et al. |

FOREIGN PATENT DOCUMENTS

| | | |
|---|---|---|
| TW | I569010 B | 2/2017 |
| WO | WO 2012/105171 A1 | 8/2012 |

* cited by examiner

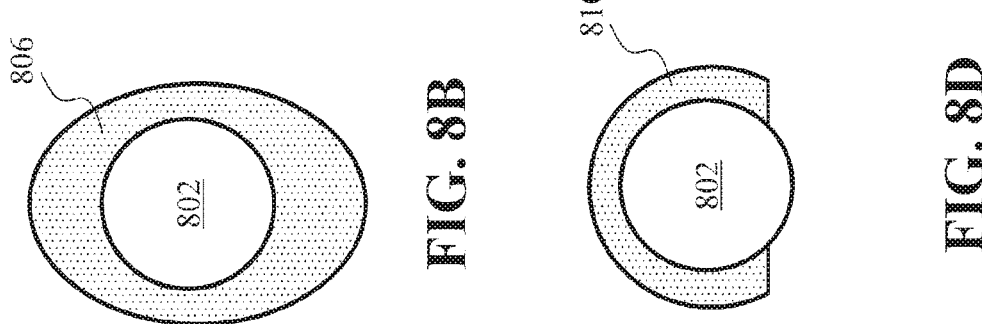
FIG. 8B
FIG. 8D
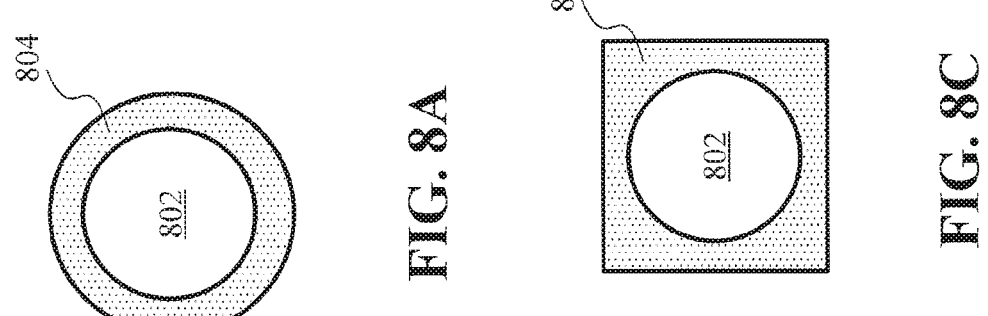
FIG. 8A
FIG. 8C

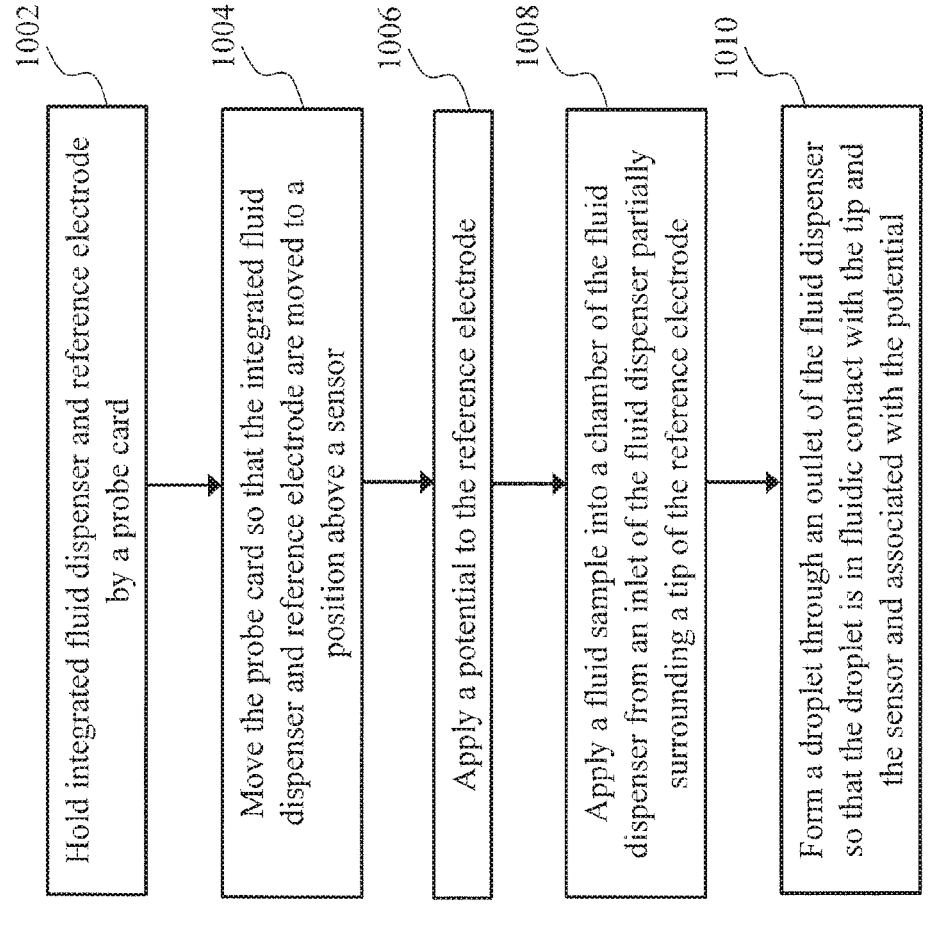

1002

1004

1006

1008

1010

Hold integrated fluid dispenser and reference electrode by a probe card

Move the probe card so that the integrated fluid dispenser and reference electrode are moved to a position above a sensor Apply a potential to the reference electrode Apply a fluid sample into a chamber of the fluid dispenser from an inlet of the fluid dispenser partially surrounding a tip of the reference electrode Form a droplet through an outlet of the fluid dispenser so that the droplet is in fluidic contact with the tip and the sensor and associated with the potential

INTEGRATED REFERENCE ELECTRODE AND FLUID DISPENSER

CROSS REFERENCE TO RELATED APPLICATION

This application is a continuation of U.S. patent application Ser. No. 15/725,776, titled "Integrated Reference Electrode and Fluid dispenser," which was filed on Oct. 5, 2017, which claims the benefit of U.S. Provisional Patent Application No. 62/491,809, titled "Integrated Reference Electrode and Fluid dispenser," which was filed on Apr. 28, 2017, and the disclosures of which are incorporated by reference herein in their entirety.

BACKGROUND

Biosensors are devices for sensing and detecting biomolecules and operate on the basis of electronic, electrochemical, optical, and mechanical detection principles. Biosensors that include transistors are sensors that electrically sense charges, photons, and mechanical properties of bio-entities or biomolecules. The sensing can be performed by detecting the bio-entities or biomolecules themselves or through interaction and reaction between specified reactants and bio-entities/biomolecules. Using semiconductor processes, such biosensors can be manufactured as integrated circuits (ICs) and/or microelectromechanical system (MEMS).

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIGS. 8A-8D illustrate cross-sections of various exemplary apparatuses each including an integrated reference electrode and a fluid dispenser, according to some embodiments.

FIG. 10 is a flow diagram of an exemplary method of using the apparatus including an integrated reference electrode and a fluid dispenser, according to some embodiments.

DETAILED DESCRIPTION

Figure 1:
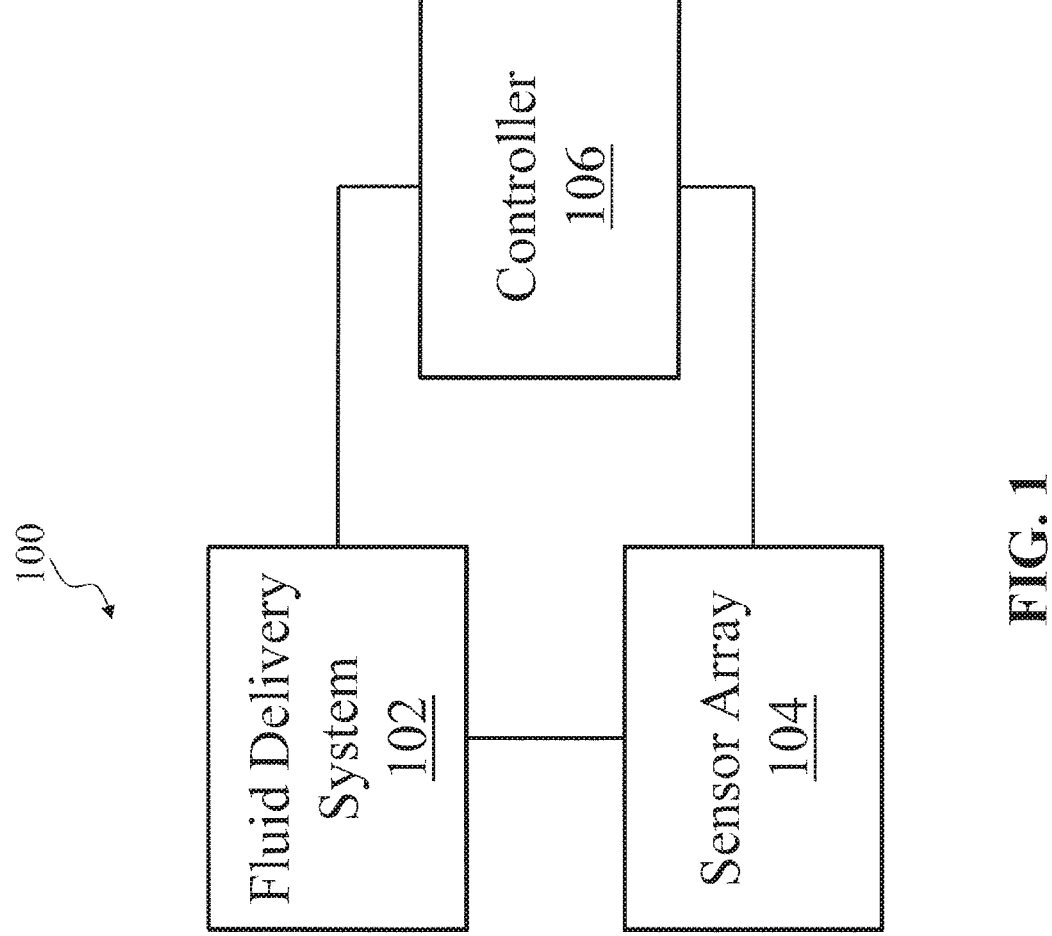
FIG. 1 is a diagram illustrating components of a biosensor testing platform, according to some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over a second feature in the description that follows may include embodiments in which the first and second features are formed in direct contact, and may also include embodiments in which additional features may be formed and/or disposed between the first and second features, such that the first and second features may not be in direct contact. In addition, the present disclosure may repeat reference numerals and/or letters in the various examples. This does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (e.g., rotated 90 degrees or at other orientations) and the spatially relative descriptors used herein may likewise be interpreted accordingly.

Terminology

Unless defined otherwise, all technical and scientific terms used herein have the same meanings as commonly understood by one of ordinary skill in the art to which this disclosure belongs. Although any methods and materials similar or equivalent to those described herein can be used in the practice or testing of embodiments in accordance with the disclosure; the methods, devices, and materials are now described. All patents and publications mentioned herein are incorporated herein by reference for the purpose of describing and disclosing the materials and methodologies which are reported in the publications which might be used in connection with the present disclosure.

The acronym "FET," as used herein, refers to a field effect transistor. A type of FET is a metal oxide semiconductor field effect transistor (MOSFET). MOSFETs can have planar structures built in and on the planar surface of a substrate such as a semiconductor wafer. MOSFETs can also be three dimensional such as fin-based MOSFET structures.

The term "BioFET" refers to a FET that includes a layer of immobilized capture reagents that act as surface receptors to detect the presence of a target analyte of biological origin. A BioFET is a field-effect sensor with a semiconductor transducer, according to some embodiments. One advantage of BioFETs is the prospect of label-free operation. Specifically, BioFETs enable the avoidance of costly and time-consuming labeling operations such as the labeling of an analyte with, for instance, fluorescent or radioactive probes. One specific type of BioFET described herein is a dual-gate back-side sensing BioFET. The analytes for detection by a BioFET will normally be of biological origin, such as—without limitation—proteins, carbohydrates, lipids, tissue fragments, or portions thereof. A BioFET is part of a broader genus of FET sensors that may also detect any chemical compound (known in the art as a "ChemFET"). BioFETs can also detect ions such as protons or metallic ions (known in the art as an ISFET). The present disclosure applies to all types of FET-based sensors ("FET sensor"). One specific type of FET sensor herein is a Dual-Gate Back Side Sensing FET sensor ("DG BSS FET sensor").

"S/D" refers to the source/drain junctions that form two of the four terminals of a FET.

The expression "high-k" refers to a high dielectric constant. In the field of semiconductor device structures and manufacturing processes, high-k refers to a dielectric constant that is greater than the dielectric constant of $SiO_2$ (i.e., greater than 3.9).

The term "analysis" generally refers to a process or step involving physical, chemical, biochemical, or biological analysis that includes, but is not limited to, characterization, testing, measurement, optimization, separation, synthesis, addition, filtration, dissolution, or mixing.

The term "assay" generally refers to a process or step involving the analysis of a chemical or a target analyte and includes, but is not limited to, cell-based assays, biochemical assays, high-throughput assays and screening, diagnostic assays, pH determination, nucleic acid hybridization assays, polymerase activity assays, nucleic acid and protein sequencing, immunoassays (e.g., antibody-antigen binding assays, enzyme-linked immunosorbent assays, and immunoquantitative polymerase chain reaction), bisulfite methylation assays for detecting methylation pattern of genes, protein assays, protein binding assays (e.g., protein-protein, protein-nucleic acid, and protein-ligand binding assays), enzymatic assays, coupled enzymatic assays, kinetic measurements (e.g., kinetics of protein folding and enzymatic reaction kinetics), enzyme inhibitor and activator screening, chemiluminescence and electrochemiluminescence assays, fluorescent assays, fluorescence polarization and anisotropy assays, absorbance and colorimetric assays (e.g., Bradford assay, Lowry assay, Hartree-Lowry assay, Biuret assay, and BCA assay), chemical assays (e.g., for the detection of environmental pollutants and contaminants, nanoparticles, or polymers), and drug discovery assays. The apparatus, systems, and methods described herein may use or adopt one or more of these assays to be used with any of the FET sensor described designs.

The term "liquid biopsy" generally refers to a biopsy sample obtained from a subject's bodily fluid as compared to a subject's tissue sample. The ability to perform assays using a body fluid sample is oftentimes more desirable than using a tissue sample. The less invasive approach of using a body fluid sample has wide ranging implications in terms of patient welfare, the ability to conduct longitudinal disease monitoring, and the ability to obtain expression profiles even when tissue cells are not easily accessible, e.g., in the prostate gland. Assays used to detect target analytes in liquid biopsy samples include, but are not limited to, those described above. As a non-limiting example, a circulating tumor cell (CTC) assay can be conducted on a liquid biopsy sample.

For example, a capture reagent (e.g., an antibody) immobilized on a FET sensor may be used for detection of a target analyte (e.g., a tumor cell marker) in a liquid biopsy sample using a CTC assay. CTCs are cells that have shed into the vasculature from a tumor and circulate, e.g., in the bloodstream. Generally, CTCs are present in circulation in extremely low concentrations. To assay the CTCs, CTCs are enriched from patient blood or plasma by various techniques known in the art. CTCs may be stained for specific markers using methods known in the art including, but not limited to, cytometry (e.g., flow cytometry)-based methods and immunohistochemistry-based methods. For the apparatus, systems, and methods described herein, CTCs may be captured or detected using a capture reagent. In another example, the nucleic acids, proteins, or other cellular milieu from the CTCs may be targeted as target analytes for binding to, or detection by, a capture reagent.

An increase in target analyte expressing or containing CTCs may help identify the subject as having a cancer that is likely to respond to a specific therapy (e.g., one associated with the target analyte) or allow for optimization of a therapeutic regimen with, e.g., an antibody to the target analyte. CTC measurement and quantitation can provide information on, e.g., the stage of tumor, response to therapy, disease progression, or a combination thereof. The information obtained from detecting the target analyte on the CTC can be used, e.g., as a prognostic, predictive, or pharmacodynamic biomarker. In addition, CTCs assays for a liquid biopsy sample may be used either alone or in combination with additional tumor marker analysis of solid biopsy samples.

The term "identification" generally refers to the process of determining the identity of a target analyte based on its binding to a capture reagent whose identity is known.

The term "measurement" generally refers to the process of determining the amount, quantity, quality, or property of a target analyte based on its binding to a capture reagent.

The term "quantitation" generally refers to the process of determining the quantity or concentration of a target analyte based on its binding to a capture reagent.

The term "detection" generally refers to the process of determining the presence or absence of a target analyte based on its binding to a capture reagent. Detection includes but is not limited to identification, measurement, and quantitation.

The term "chemical" refers to a substance, compound, mixture, solution, emulsion, dispersion, molecule, ion, dimer, macromolecule such as a polymer or protein, biomolecule, precipitate, crystal, chemical moiety or group, particle, nanoparticle, reagent, reaction product, solvent, or fluid any one of which may exist in the solid, liquid, or gaseous state, and which is typically the subject of an analysis.

The term "reaction" refers to a physical, chemical, biochemical, or biological transformation that involves at least one chemical and that generally involves (in the case of chemical, biochemical, and biological transformations) the breaking or formation of one or more bonds such as covalent, noncovalent, van der Waals, hydrogen, or ionic bonds. The term "reaction" includes typical chemical reactions such as synthesis reactions, neutralization reactions, decomposition reactions, displacement reactions, reduction-oxidation reactions, precipitation, crystallization, combustion reactions, and polymerization reactions, as well as covalent and noncovalent binding, phase change, color change, phase formation, crystallization, dissolution, light emission, changes of light absorption or emissive properties, temperature change or heat absorption or emission, conformational change, and folding or unfolding of a macromolecule such as a protein.

"Capture reagent," as used herein, is a molecule or compound capable of binding the target analyte or target reagent, which can be directly or indirectly attached to a substantially solid material. The capture reagent can be a chemical, and specifically any substance for which there exists a naturally occurring target analyte (e.g., an antibody, polypeptide, DNA, RNA, cell, virus, etc.) or for which a target analyte can be prepared, and the capture reagent can bind to one or more target analytes in an assay.

"Target analyte," as used herein, is the substance to be detected in the test sample using the present disclosure. The target analyte can be a chemical, and specifically any substance for which there exists a naturally occurring capture reagent (e.g., an antibody, polypeptide, DNA, RNA, cell, virus, etc.) or for which a capture reagent can be prepared, and the target analyte can bind to one or more capture reagents in an assay. "Target analyte" also includes any antigenic substances, antibodies, and combinations thereof. The target analyte can include a protein, a peptide, an amino acid, a carbohydrate, a hormone, a steroid, a vitamin, a drug including those administered for therapeutic purposes as well as those administered for illicit purposes, a bacterium, a virus, and metabolites of or antibodies to any of the above substances.

"Test sample," as used herein, means the composition, solution, substance, gas, or liquid containing the target analyte to be detected and assayed using the present disclosure. The test sample can contain other components besides the target analyte, can have the physical attributes of a liquid, or a gas, and can be of any size or volume, including for example, a moving stream of liquid or gas. The test sample can contain any substances other than the target analyte as long as the other substances do not interfere with the binding of the target analyte with the capture reagent or the specific binding of the first binding member to the second binding member. Examples of test samples include, but are not limited to, naturally-occurring and non-naturally occurring samples or combinations thereof. Naturally-occurring test samples can be synthetic or synthesized. Naturally-occurring test samples include body or bodily fluids isolated from anywhere in or on the body of a subject including, but not limited to, blood, plasma, serum, urine, saliva or sputum, spinal fluid, cerebrospinal fluid, pleural fluid, nipple aspirates, lymph fluid, fluid of the respiratory, intestinal and genitourinary tracts, tear fluid, saliva, breast milk, fluid from the lymphatic system, semen, cerebrospinal fluid, intra-organ system fluid, ascitic fluid, tumor cyst fluid, amniotic fluid, and combinations thereof. Naturally-occurring test samples can also include environmental samples such as ground water or waste water, soil extracts, air, pesticide residues, or food-related samples.

Detected substances can include, e.g., nucleic acids (including DNA and RNA), hormones, different pathogens (including a biological agent that causes disease or illness to its host, such as a virus (e.g., H7N9 or HIV), a protozoan (e.g., Plasmodium-causing malaria), or a bacteria (e.g., *E. coli* or *Mycobacterium tuberculosis*), proteins, antibodies, various drugs or therapeutics or other chemical or biological substances, including hydrogen or other ions, non-ionic molecules or compounds, polysaccharides, small chemical compounds such as chemical combinatorial library members, and the like. Detected or determined parameters may include but are not limited to, e.g., pH changes, lactose changes, changing concentration, particles per unit time where a fluid flows over the device for a period of time to detect particles, e.g., particles that are sparse, and other parameters.

As used herein, the term "immobilized," when used with respect to, e.g., a capture reagent, includes substantially attaching the capture reagent at a molecular level to a surface. For example, a capture reagent may be immobilized to a surface of the substrate material using adsorption techniques including non-covalent interactions (e.g., electrostatic forces, van der Waals, and dehydration of hydrophobic interfaces) and covalent binding techniques where functional groups or linkers facilitate attaching the capture reagent to the surface. Immobilizing a capture reagent to a surface of a substrate material may be based upon the properties of the substrate surface, the medium carrying the capture reagent, and the properties of the capture reagent. In some cases, a substrate surface may be first modified to have functional groups bound to the surface. The functional groups may then bind to biomolecules or biological or chemical substances to immobilize them thereon.

The term "nucleic acid" generally refers to a set of nucleotides connected to each other via phosphodiester bond and refers to a naturally occurring nucleic acid to which a naturally occurring nucleotide existing in nature is connected, such as DNA comprising deoxyribonucleotides having any of adenine, guanine, cytosine, and thymine connected to each other and/or RNA comprising ribonucleotides having any of adenine, guanine, cytosine, and uracil connected to each other. In addition, non-naturally occurring nucleotides and non-naturally occurring nucleic acids are within the scope of the nucleic acid of the present disclosure. Examples include peptide nucleic acids (PNA), peptide nucleic acids with phosphate groups (PHONA), bridged nucleic acids/locked nucleic acids (BNA/LNA), and morpholino nucleic acids. Further examples include chemically-modified nucleic acids and nucleic acid analogues, such as methylphosphonate DNA/RNA, phosphorothioate DNA/RNA, phosphoramidate DNA/RNA, and 2'-O-methyl DNA/RNA. Nucleic acids include those that may be modified. For example, a phosphoric acid group, a sugar, and/or a base in a nucleic acid may be labeled as necessary. Any substances for nucleic acid labeling known in the art can be used for labeling. Examples thereof include but are not limited to radioactive isotopes (e.g., 32P, 3H, and 14C), DIG, biotin, fluorescent dyes (e.g., FITC, Texas, cy3, cy5, cy7, FAM, HEX, VIC, JOE, Rox, TET, Bodipy493, NBD, and TAMRA), and luminescent substances (e.g., acridinium ester).

"Aptamer" as used herein refers to oligonucleic acids or peptide molecules that bind to a specific target molecule. The concept of using single-stranded nucleic acids (aptamers) as affinity molecules for protein binding is based on the ability of short sequences to fold, in the presence of a target, into unique, three-dimensional structures that bind the target with high affinity and specificity. Aptamers can be oligo-nucleotide ligands that are selected for high-affinity binding to molecular targets.

The term "antibody" as used herein refers to a polypeptide of the immunoglobulin family that is capable of binding a corresponding antigen non-covalently, reversibly, and in a specific manner. For example, a naturally occurring IgG antibody is a tetramer including at least two heavy (H) chains and two light (L) chains inter-connected by disulfide bonds. Each heavy chain includes a heavy chain variable region (abbreviated herein as VH) and a heavy chain constant region. The heavy chain constant region includes three domains: CH1, CH2 and CH3. Each light chain includes a light chain variable region (abbreviated herein as VL) and a light chain constant region. The light chain constant region includes one domain, CL. The VH and VL regions can be further subdivided into regions of hypervariability, termed complementarity determining regions (CDR), interspersed with regions that are more conserved, termed framework regions (FR). Each VH and VL includes three CDRs and four FRs arranged from amino-terminus to carboxy-terminus in the following order: FR1, CDR1, FR2, CDR2, FR3, CDR3, and FR4. The three CDRs constitute about 15-20% of the variable domains. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antibody" includes, but is not limited to, monoclonal antibodies, human antibodies, humanized antibodies, chimeric antibodies, and anti-idiotypic (anti-Id) antibodies including, e.g., anti-Id antibodies to antibodies of the present disclosure. The antibodies can be of any isotype/ class (e.g., IgG, IgE, IgM, IgD, IgA, and IgY), or subclass (e.g., IgG1, IgG2, IgG3, IgG4, IgA1, and IgA2).

The term "polymer" means any substance or compound that is composed of two or more building blocks ('mers') that are repetitively linked to each other. For example, a "dimer" is a compound in which two building blocks have been joined together. Polymers include both condensation and addition polymers. Examples of condensation polymers include polyamide, polyester, protein, wool, silk, polyurethane, cellulose, and polysiloxane. Examples of addition polymers are polyethylene, polyisobutylene, polyacrylonitrile, poly(vinyl chloride), and polystyrene. Other examples include polymers having enhanced electrical or optical properties (e.g., a nonlinear optical property) such as electroconductive or photorefractive polymers. Polymers include both linear and branched polymers.

Overview of Exemplary Biosensing Testing Platform

FIG. 1 illustrates an overview of components that may be included in a biosensor testing platform 100, according to some embodiments. Biosensor testing platform 100 includes a fluid delivery system 102, a sensor array 104, and a controller 106. Fluid delivery system 102 can deliver one or more fluid samples to a sensor array 104. Controller 106 may be used to send and receive electrical signals to sensor array 104 to perform a bio or chemical sensor measurement. Controller 106 may also be used to send electrical signals to fluid delivery system 102 to, for example, actuate one or more valves, pumps, and/or motors. In another example, different controllers may be used to communicate with fluid delivery system 102 and sensor array 104.

Fluid delivery system 102 may include a variety of components designed to deliver controlled amounts of fluid to one or more sensors within sensor array 104. Each fluid may be delivered for a different purpose. For example, a first fluid may be delivered to functionalize a surface of one or more sensors in sensor array 104 with capture reagents. A second (and different) fluid may be delivered to provide target reagents to be captured by the capture reagents. Other fluids may be delivered to wash the sensor surface or provide a controlled buffer solution for performing the sensor measurement.

Fluid delivery system 102 may include one or more chambers for holding the various fluids to be delivered to sensor array 104. Additionally, fluid delivery system 102 may include a network of fluidic channels for directing the various fluids to specific locations either within fluid delivery system 102 or towards sensor array 104. In order to control the flow of the fluids, fluid delivery system 102 may include one or more valves, pumps, and/or motors to provide a pressure differential or force on the fluid and cause it to flow. Some of the components of fluid delivery system 102 may be easily disposable and replaceable, allowing for the same fluid delivery system 102 to be used for multiple chemical or biological tests without contamination. Fluid delivery system 102 may be a handheld device having its own controller. An example fluid delivery system including integrated reference electrode and fluid dispenser is described in further detail later with reference to FIGS. 6-9.

Sensor array 104 may include an array of BioFETs where one or more of the BioFETs in the array are functionalized to detect a particular target analyte. Different ones of the BioFETs may be functionalized using different capture reagents (for detecting different target analytes.) Further details regarding an example design of particular BioFETs and an example of the arrayed architecture is provided below.

Controller 106 may include one or more processing devices, such as a microprocessor, and may be programmable to control the operation of fluidic delivery system 102 and/or sensor array 104. In some embodiments, fluidic delivery system 102 and sensor array 104 each has its own programmable controller. The electrical signals that may be sent from and received by sensor array 104 will be discussed in more detail below.

Details regarding the design and operation of sensor array 104 is provided first, followed by details on an example fluidic testing platform that utilizes an integrated reference electrode and fluid dispenser to accurately deliver fluid to a sensor area and apply a potential to the fluid sample. The example fluidic testing platform thus can reduce the high-accuracy positioning requirement for an alignment between the fluid dispenser and the reference electrode. Moreover, self-cleaning of the reference electrode can be achieved by the subsequent test samples without the need of an additional cleaning step using a washing solution.

Dual Gate Back-Side FET Sensors

In some embodiments, sensor array 104 can include an array of BioFET sensors. One example type of BioFET sensor is a dual gate back-side FET sensor. Dual gate back-side FET sensors utilize semiconductor manufacturing techniques and biological capture reagents to form arrayed sensors. The dual gate back-side sensing FET sensor has two gate electrodes each of which is connected to a different electrical node. A first one of the two gate electrodes is referred to herein as a "front-side gate" and the second one of the two gate electrodes is referred to herein as a "back-side gate." Both the front-side gate and the back-side gate are configured such that, in operation, each one may be electrically charged and/or discharged, each thereby influencing an electric field between the source/drain terminals of the dual gate back-side sensing FET sensor. The front-side gate is electrically conductive, separated from a channel region by a front-side gate dielectric, and configured to be charged and discharged by an electrical circuit to which it is coupled. The back-side gate is separated from the channel region by a back-side gate dielectric and includes a biofunctionalized sensing layer disposed on the back-side gate dielectric. The amount of electric charge on the back-side gate is a function of whether a biorecognition reaction has occurred. In operation, the front-side gate is charged to a voltage within a predetermined range of voltages. The voltage on the front-side gate determines a corresponding conductivity of the FET sensor's channel region. A change in the electric charge on the back-side gate changes the conductivity of the channel region. This change in conductivity indicates a biorecognition reaction.

One advantage of FET sensors is the prospect of label-free operation. Specifically, FET sensors enable the avoidance of costly and time-consuming labeling operations such as the labeling of an analyte with, for instance, fluorescent or radioactive probes.

Figure 2:
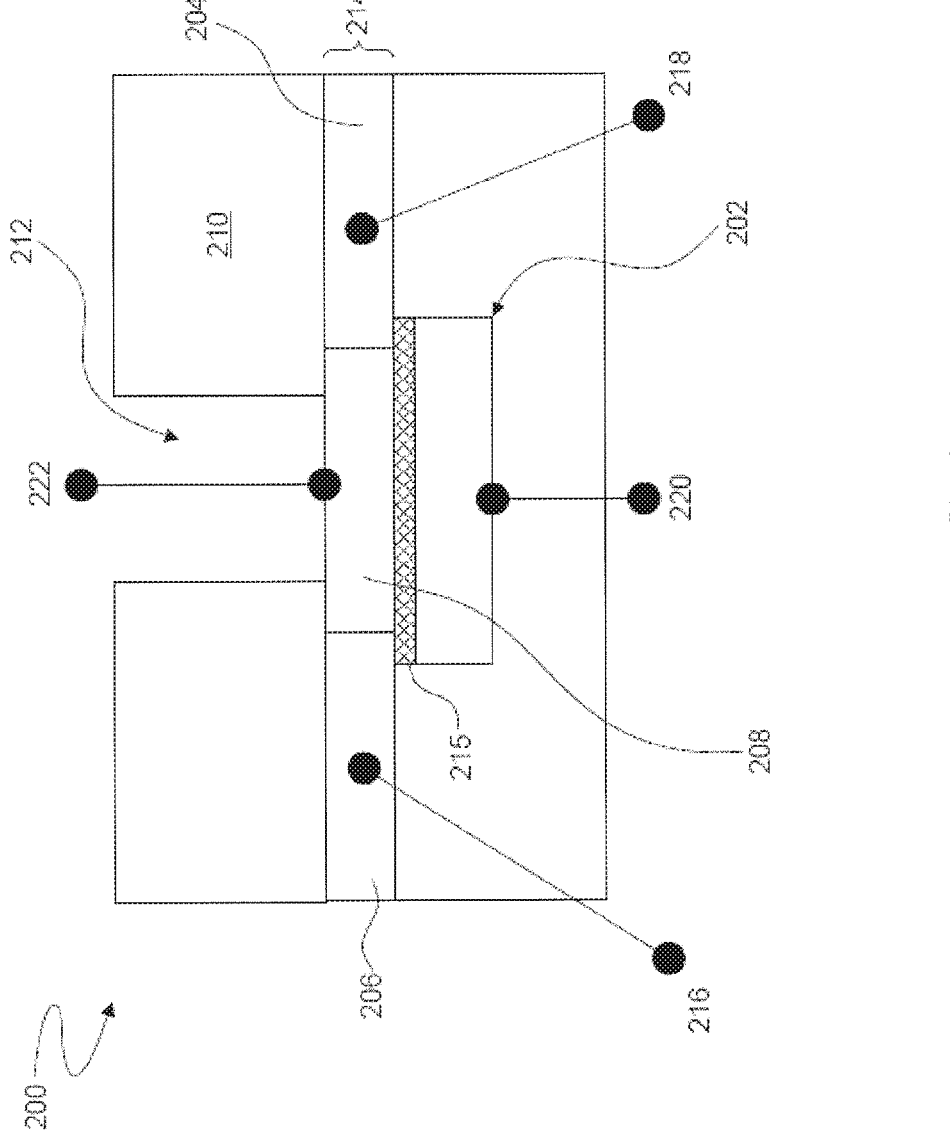
FIG. 2 is a cross-sectional view of an exemplary dual-gate back-side sensing FET sensor, according to some embodiments.

Referring to FIG. 2, illustrated is an exemplary dual gate back-side sensing FET sensor 200. Dual gate back-side sensing FET sensor 200 includes a control gate 202 formed over substrate 214 and separated therefrom by an intervening dielectric 215 disposed on substrate 214. Substrate 214 further includes a source region 204, a drain region 206, and a channel region 208 between source region 204 and drain region 206. In some embodiments, substrate 214 has a thickness between about 100 nm and about 130 nm. Gate 202, source region 204, drain region 206, and channel region 208 may be formed using suitable CMOS process technology to form a FET. An isolation layer 210 is disposed on the opposing side of substrate 214 from gate 202. In some embodiments, isolation layer 210 has a thickness of about 1 μm. In this disclosure the side of substrate 214 over which gate 202 is disposed is referred to as the "front-side" of substrate 214. Similarly, the side of substrate 214 on which isolation layer 210 is disposed is referred to as the "back-side."

An opening 212 is provided in isolation layer 210. Opening 212 may be substantially aligned with gate 202. In other embodiments, opening 212 is larger than gate 202 and may extend over multiple dual gate back-side sensing FET sensors. An interface layer (not shown) may be disposed in opening 212 on the surface of channel region 208. The interface layer may be operable to provide an interface for positioning and immobilizing one or more receptors for detection of biomolecules or bio-entities. Further details regarding the interface layer are provided below.

Dual gate back-side sensing FET sensor 200 includes electrical contacts to drain region 206 (Vd 216), source region 204 (Vs 218), gate structure 202 (front-side gate 220), and/or active region 208 (e.g., back-side gate 222). It should be noted that back-side gate 222 does not need to physically contact substrate 214 or any interface layer over substrate 214. Thus, while a conventional FET uses a gate contact to control conductance of the transistor between the source and drain (e.g., the channel), dual gate back-side sensing FET sensor 200 allows receptors formed on a side opposing gate structure 202 of the FET device to control the conductance, while gate structure 202 provides another gate to control the conductance. With this dual gate arrangement, dual gate back-side sensing FET sensor 200 may be used to detect one or more specific biomolecules or bio-entities in the environment around and/or in opening 212, as discussed in more detail below.

Dual gate back-side sensing FET sensor 200 may be connected to additional passive components such as resistors, capacitors, inductors, and/or fuses. Dual gate back-side sensing FET sensor 200 may also be connected to other active components, including P-channel field effect transistors (PFETs), N-channel field effect transistors (NFETs), metal-oxide-semiconductor field effect transistors (MOSFETs), high voltage transistors, and/or high frequency transistors; other suitable components; and/or combinations thereof. It is further understood that additional features can be added in dual gate back-side sensing FET sensor 200, and some of the features described can be replaced or eliminated, for additional embodiments of dual gate back-side sensing FET sensor 200.

Figure 3:
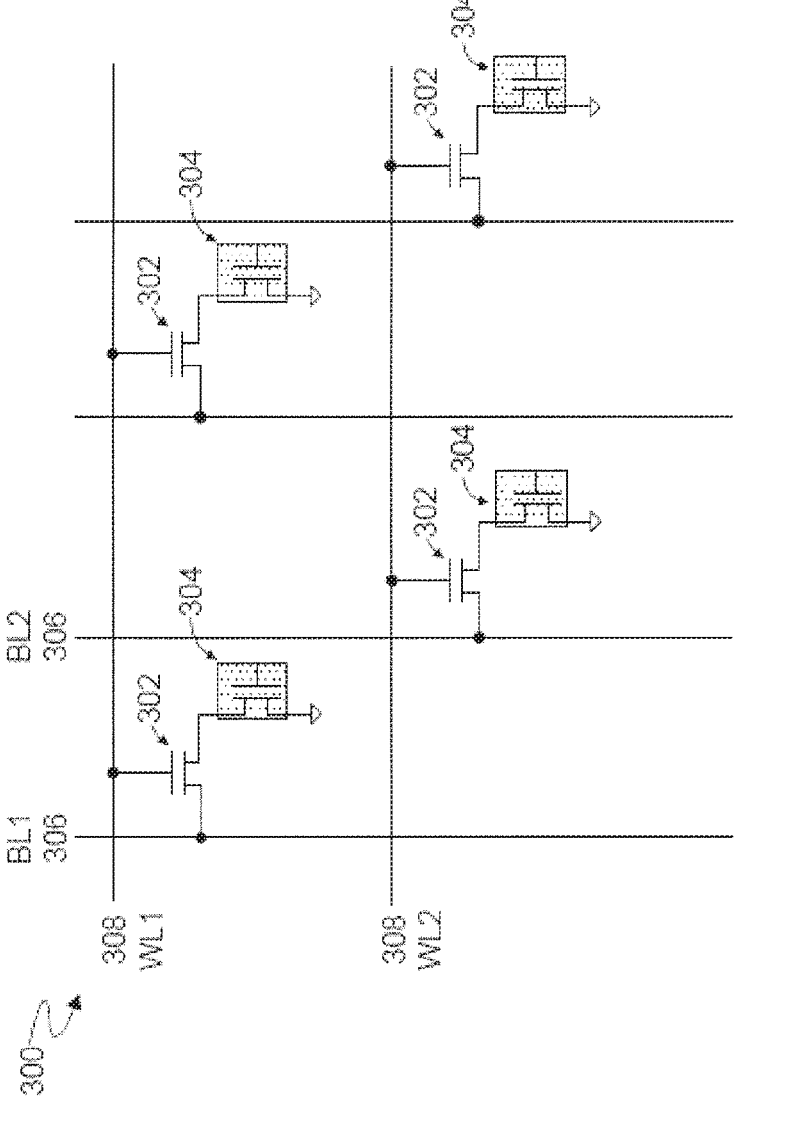
FIG. 3 is a circuit diagram of a plurality of FET sensors configured in an exemplary addressable array, according to some embodiments.

Referring to FIG. 3, illustrated is a schematic of a portion of an exemplary addressable array 300 of FET sensors 304 connected to bit lines 306 and word lines 308. It is noted that the terms bit lines and word lines are used herein to indicate similarities to array construction in memory devices, however, there is no implication that memory devices or a storage array necessarily be included in the array. Addressable array 300 may have similarities to that employed in other semiconductor devices such as dynamic random access memory (DRAM) arrays. For example, dual gate back-side sensing FET sensor 200, described above with reference to FIG. 2, may be formed in a position that a capacitor would be found in a DRAM array. Schematic 300 is exemplary only and one would recognize other configurations are possible.

FET sensors 304 may each be substantially similar to dual gate back-side sensing FET sensor 200 according to some embodiments. FETs 302 are configured to provide connection between a drain terminal of FET sensor 304 and bit line 306. In this way, FETs 302 are analogous to access transistors in a DRAM array. In some embodiments, FET sensors 304 are dual gate back-side sensing FET sensors and each include a sensing gate provided by a receptor material disposed on a dielectric layer overlying a FET active region disposed at a reaction site, and a control gate provided by a gate electrode (e.g., polysilicon) disposed on a dielectric layer overlying the FET active region.

Addressable array 300 shows an array formation designed to detect small signal changes provided by biomolecules or bio-entities introduced to FET sensors 304. The arrayed format using bit lines 306 and word lines 308 allows for a decreased number of input/output pads since common terminals of different FETs in the same row or column are tied together. Amplifiers may be used to enhance the signal strength to improve the detection ability of the device having the circuit arrangement of schematic 300. In some embodiments, when voltage is applied to particular word lines 308 and bit lines 306, the corresponding access transistors 302 will be turned on (e.g., like a switch). When the gate of the associated FET sensor 304 (e.g., such as back-side gate 222 of the dual gate back-side sensing FET sensor 200) has its charge affected by the bio-molecule presence, a threshold voltage of FET sensor 304 is changed, thereby modulating the current (e.g., $I_{ds}$) for a given voltage applied to back-side gate 222. The change of the current (e.g., $I_{ds}$) or threshold voltage ($V_t$) can serve to indicate detection of the relevant biomolecules or bio-entities.

Figure 4:
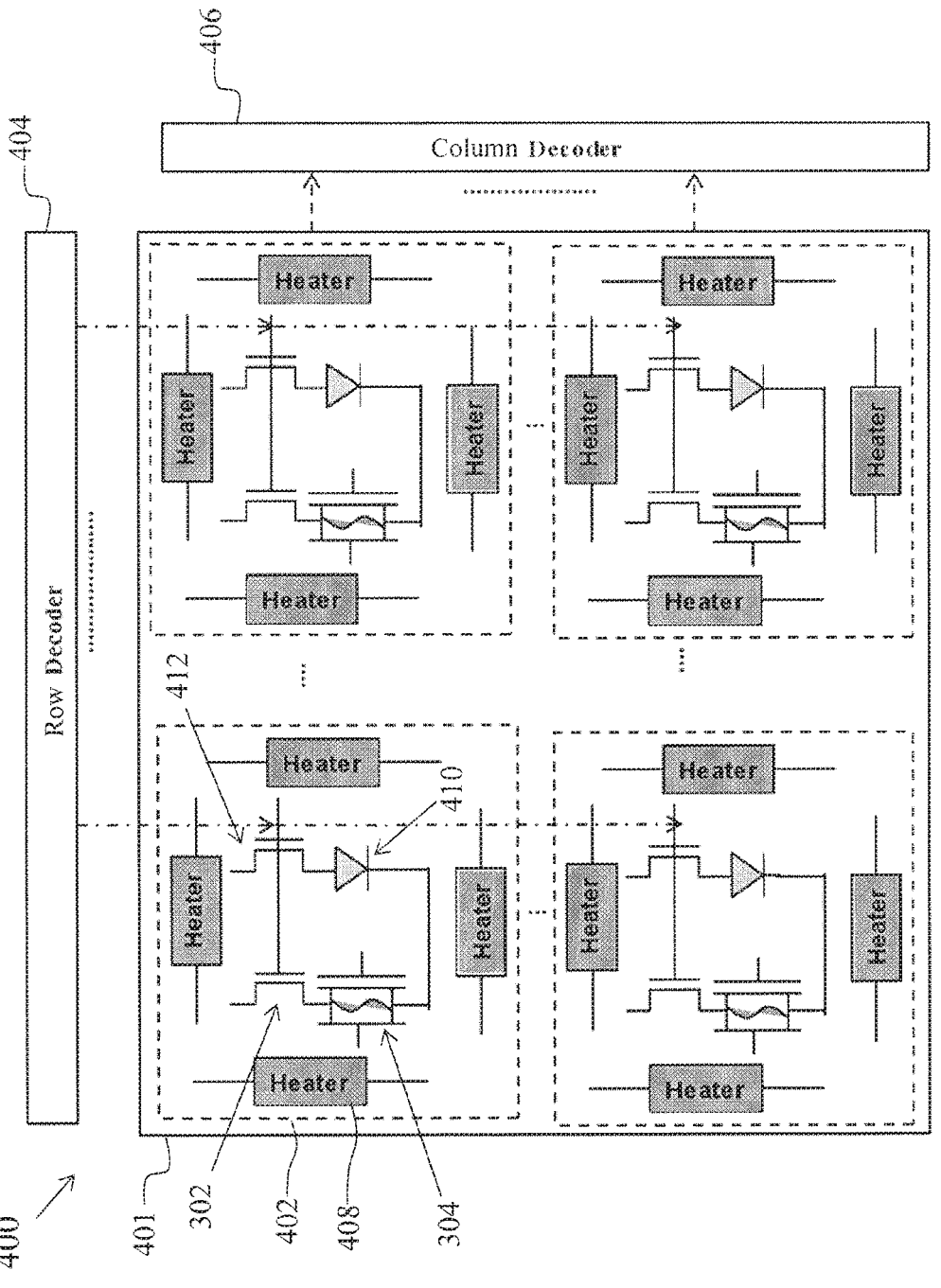
FIG. 4 is a circuit diagram of an exemplary addressable array of dual gate FET sensors and heaters, according to some embodiments.

Referring to FIG. 4, an exemplary schematic 400 is presented. Exemplary schematic 400 includes access transistor 302 and FET sensor 304 arranged as an array 401 of individually addressable pixels 402. Array 401 may include any number of pixels 402. For example, array 401 may include 128×128 pixels. Other arrangements may include 256×256 pixels or non-square arrays such as 128×256 pixels.

Each pixel 402 includes access transistor 302 and FET sensor 304 along with other components that may include one or more heaters 408 and a temperature sensor 410. In this example, access transistor 302 is an n-channel FET. An n-channel FET 412 may also act as an access transistor for temperature sensor 410. In some embodiments, the gates of FETs 302 and 412 are connected, though this is not required. Each pixel 402 (and its associated components) may be individually addressed using column decoder 404 and row decoder 406. In some embodiments, each pixel 402 has a size of about 10 micrometers by about 10 micrometers. In some embodiments, each pixel 402 has a size of about 5 micrometers by about 5 micrometers or has a size of about 2 micrometers by about 2 micrometers.

Column decoder 406 and row decoder 404 may be used to control the ON/OFF state of n-channel FETs 302 and 412. Turning on n-channel FET 302 provides a voltage to an S/D region of dual gate back-side sensing FET sensor 304. When FET sensor 304 is ON, a current $I_{ds}$ flows through FET sensor 304 and may be measured.

Heater 408 may be used to locally increase a temperature around a dual gate back-side sensing FET sensor 304. Heater 408 may be constructed using any known technique, such as forming a metal pattern with a high current running through it. Heater 408 may also be a thermoelectric heater/cooler, like a Peltier device. Heater 408 may be used during certain biological tests such as to denature DNA or RNA or to provide a binding environment for certain biomolecules. Temperature sensor 410 may be used to measure the local temperature around dual gate back-side sensing FET sensor 304. In some embodiments, a control loop may be created to control the temperature using heater 408 and the feedback received from temperature sensor 410. In some embodiments, heater 408 may be a thermoelectric heater/cooler that allows for local active cooling of the components within pixel 402.

Figure 5A:
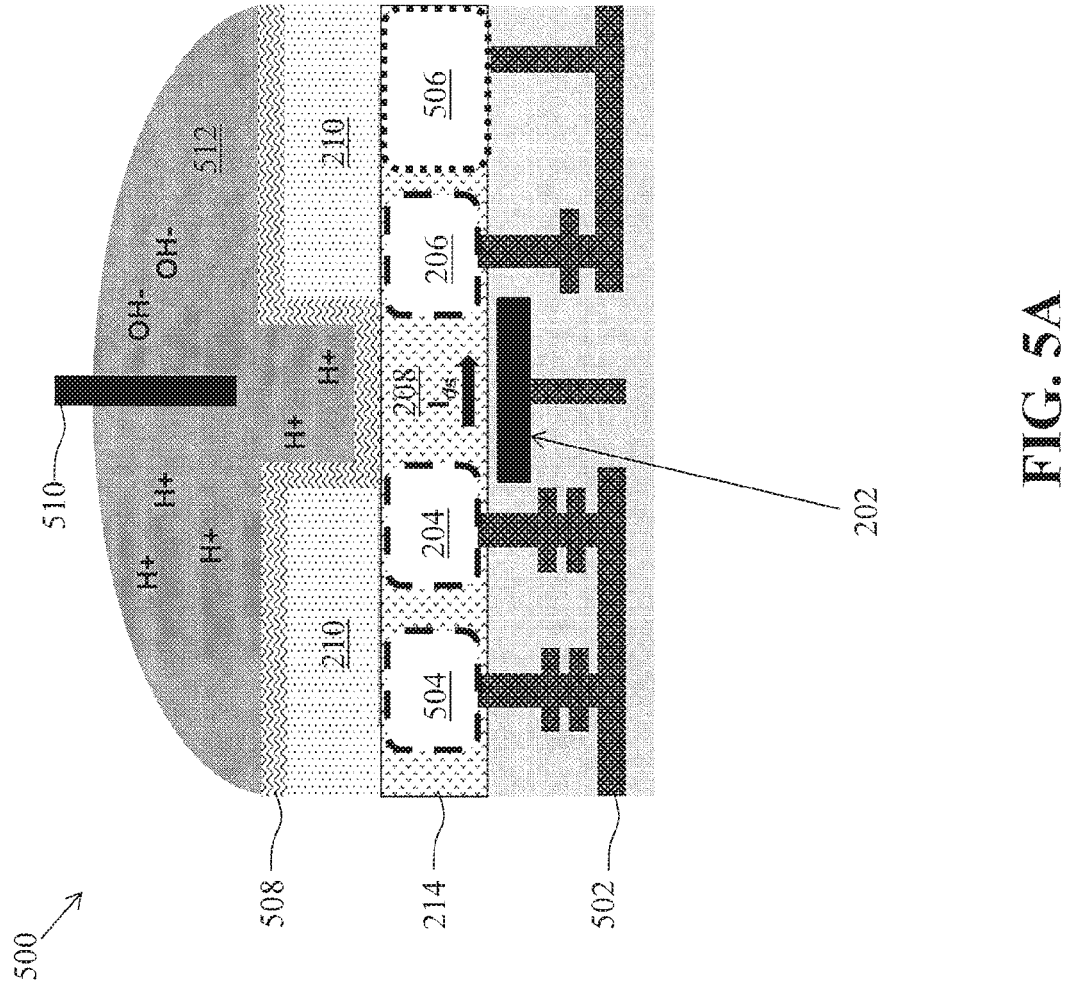
FIG. 5A is a cross-sectional view of an exemplary dual gate back-side sensing FET sensor, according to some embodiments.

Referring to FIG. 5A, a cross section of an example dual gate back-side sensing FET sensor 500 is provided. Dual gate back-side sensing FET sensor 500 is one implementation of dual gate back-side sensing FET sensor 200, which was previously described above. Elements from FIG. 2 are labeled with element numbers from FIG. 2 and their descriptions are not repeated here. Dual gate back-side sensing FET sensor 500 includes gate 202, source region 204, drain region 206, and channel region 208, where source region 204 and drain region 206 are formed within substrate 214. Gate 202, source region 204, drain region 206, and channel region 208 form a FET. It should be noted that the various components of FIG. 5A are not intended to be drawn to scale and are exaggerated for visual convenience, as would be understood by a person skilled in the relevant art.

In some embodiments, dual gate back-side sensing FET sensor 500 is coupled to various layers of metal interconnects 502 that make electrical connection with various doped regions and other devices formed within substrate 214. Metal interconnects 502 may be manufactured using fabrication processes well known to a person skilled in the relevant art.

Dual gate back-side FET sensor 500 may include a body region 504 separate from source region 204 and drain region 206. Body region 504 may be used to bias a carrier concentration in active region 208 between source region 204 and drain region 206. In some embodiments, a negative voltage bias may be applied to body region 504 to improve the sensitivity of dual gate back-side FET sensor 500. In some embodiments, body region 504 is electrically connected to source region 204. In some embodiments, body region 504 is electrically grounded.

Dual gate back-side FET sensor 500 may be coupled to additional circuitry 506 fabricated within substrate 214. Circuitry 506 may include MOSFET devices, resistors, capacitors, and/or inductors to form circuitry to aid in the operation of dual gate back-side sensing FET sensor 500. For example, column decoder 406 and row decoder 404 may be formed in circuitry 506. Circuitry 506 may include amplifiers, analog to digital converters (ADCs), digital to analog converters (DACs), voltage generators, logic circuitry, and DRAM memory. All or some of the components of additional circuitry 506 may be integrated in the same substrate 214 as dual gate back-side FET sensor 500. It should be understood that many FET sensors, each substantially similar to dual gate back-side FET sensor 500, may be integrated on substrate 214 and coupled to additional circuitry 506. In some embodiments, all or some of the components of additional circuitry 506 are provided on another semiconductor substrate separate from substrate 214. In some embodiments, some components of additional circuitry 506 are integrated in the same substrate 214 as dual gate back-side FET sensor 500, and some components of additional circuitry 506 are provided on another semiconductor substrate separate from substrate 214.

Still referring to the illustrative example of FIG. 5A, dual gate back-side sensing FET sensor 500 includes an interface layer 508 deposited over isolation layer 210 and within the opening over channel region 208. In some embodiments, interface layer 508 has a thickness between about 20 Å and about 40 Å. Interface layer 508 may be a high-K dielectric material, such as hafnium silicate, hafnium oxide, zirconium oxide, aluminum oxide, tantalum pentoxide, hafnium dioxide-alumina ($HfO_2$—$Al_2O_3$) alloy, or any combination thereof. Interface layer 508 may act as a support for the attachment of capture reagents as will be discussed in more detail later in the section directed to biological sensing. A fluid sample 512 is provided over the reaction site of dual gate back-side sensing FET sensor 500, and a fluid gate 510 is placed within fluid sample 512. Fluid sample 512 may be a buffer solution containing capture reagents, target reagents, wash solution, or any other biological or chemical species.

An example operation of dual gate back-side FET sensor 500 acting as a pH sensor will now be described. Briefly, fluid gate 510 is used to provide an electrical contact to the "second gate" of the dual gate back-side sensing FET sensor. Fluid sample 512 is provided over the reaction site of dual gate back-side sensing FET sensor 500, and fluid gate 510 is placed within fluid sample 512. The pH of the solution relates to the concentration of hydrogen ions [$H^+$] in the solution. The accumulation of the ions near the surface of interface layer 508 above channel region 208 affects the formation of an inversion layer within channel region 208 that forms a conductive pathway between source region 204 and drain region 206. This can be measured by the change in the conductivity of the FET sensor. In some embodiments, fluid gate 510 is used as the gate of the transistor during sensing while gate 202 remains floating. In some embodiments, fluid gate 510 is used as the gate of the transistor during sensing while gate 202 is biased at a given potential. For example, gate 202 may be biased at a potential between −2V and 2V depending on the application, while fluid gate 510 is swept between a range of voltages. In some embodiments, fluid gate 510 is biased at a given potential (e.g., grounded) while gate 202 is used as the gate of the transistor (e.g., its voltage is swept across a range of potentials) during sensing. In some embodiments, fluid gate 510 may be a reference electrode that can provide a stable and known electrical potential to fluid sample 512. Fluid gate 510 may be formed from platinum or may be formed from other commonly used material(s) for reference electrodes in the electrochemical analysis. The reference electrodes can be an Ag/AgCl electrode, which has a stable potential value. As described below in detail, the reference electrode of fluid gate 510 may be part of an apparatus including an integrated reference electrode and a fluid dispenser, which can deliver fluid sample 512 to the reaction site of dual gate back-side sensing FET sensor 500 accurately apply a potential set by the reference electrode to fluid sample 512 without the need of additional positioning. The continuity of the path between fluid sample 512 and fluid gate 510 can thus be ensured by the apparatus.

Figure 5C:
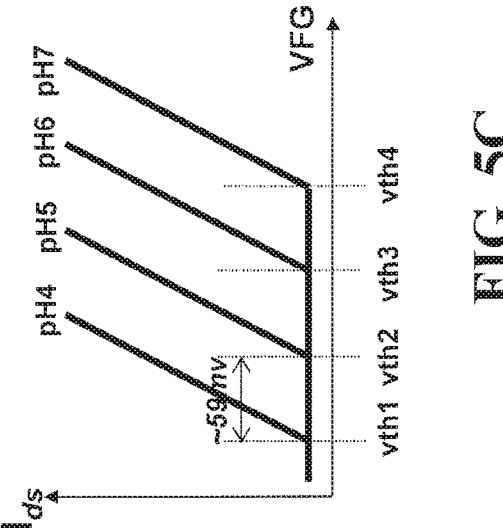
FIGS. 5B and 5C illustrate using the dual gate back-side sensing FET sensor as a pH sensor, according to some embodiments.
Figure 5B:
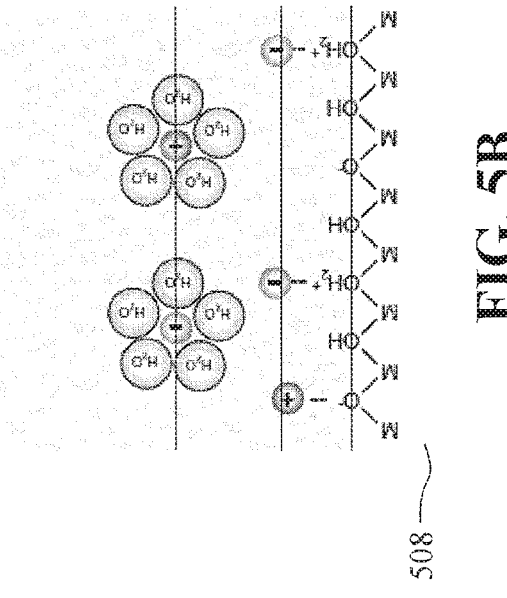

FIG. 5B shows ions in solution binding to a surface of interface layer 508. A top-most atomic layer of interface layer 508 is depicted as the various dangling [O⁻], [OH], and [OH₂⁺] bonds. As the ions accumulate on the surface, the total surface charge affects the threshold voltage of the transistor. As used herein, the threshold voltage is the minimum potential between the gate and the source of a FET sensor that is required to form a conductive path of minority carriers between the source and the drain of the FET sensor. The total charge also relates to pH of the solution, as a higher accumulation of positive charge signifies a lower pH while a higher accumulation of negative charge signifies a higher pH. FIG. 5C illustrates a change in threshold voltage that results due to different pH values in an n-channel FET sensor.

Integrated Reference Electrode and Fluid Dispenser

Referring to the example FET sensor illustration in FIG. 5A, fluid sample 512 is delivered over the sensor surface to perform the measurement. As described above, it is desired to reduce the high-accuracy positioning requirement for the alignment between fluid sample 512 applied by the fluid dispenser and fluid gate 510, e.g., the reference electrode, that is in fluidic contact with fluid sample 512. It is also desired to ensure the fluidic contact between the fluid sample 512 and fluid gate 510, e.g., the reference electrode.

Figure 6:
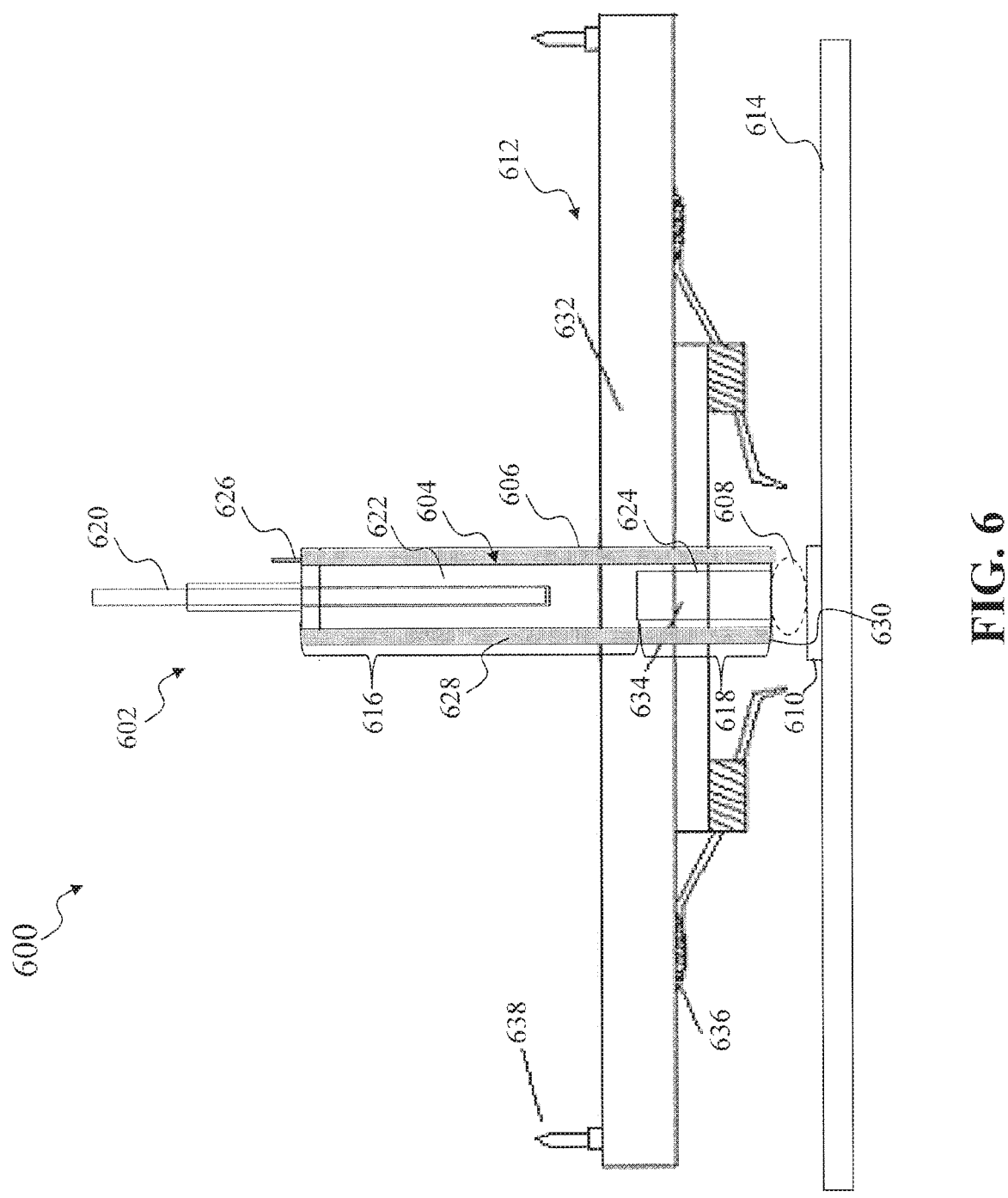
FIG. 6 illustrates an exemplary system including an integrated reference electrode and a fluid dispenser for sensor characterization, according to some embodiments.

FIG. 6 illustrates an example of a system 600, according to some embodiments. System 600 includes an apparatus 602 integrating a reference electrode 604 and a fluid dispenser 606 for delivering a droplet 608 of fluid sample to a device-under-test (DUT) 610 and applying a potential to droplet 608. System 600 can accurately align fluid dispenser 606 and reference electrode 604. Moreover, self-cleaning of reference electrode 604 can be achieved for subsequent tests without the need of an additional cleaning step using a washing solution.

In some embodiments, system 600 includes a probe card 612 configured to hold fluid dispenser 606 and reference electrode 604 so that fluid dispenser 606 and reference electrode 604 are moved together as probe card 612 moves. Probe card 612 may be an interface between an electronic test system, e.g., controller 106, and a device substrate 614 on which DUT 610 is formed.

In some embodiments, reference electrode 604 and fluid dispenser 606 (shown in grey color) are integrated together. Reference electrode 604 may be any electrode that has a stable and known potential. Examples of reference electrode 604 include, but are not limited to, an Ag/AgCl reference electrode, a Cu/Cu(II) reference electrode, a Hg/Hg(II) electrode, a saturated calomel electrode (SCE), a standard hydrogen electrode (SHE), a normal hydrogen electrode (NHE), a reversible hydrogen electrode (RHE), a dynamic hydrogen electrode (DHE), etc.

In some embodiments, reference electrode 604 includes a body 616 and a tip 618. Body 616 may be a main part of reference electrode 604 in which the stable and known electrode potential is reached by, for example, a redox reaction with constant concentrations of reactants. For example, body 616 may include a metal plug 620 and a filling solution 622 in which metal plug 620 is immersed. In some embodiments, metal plug 620 may be held by a cap at an end of body 616 so that at least a part of metal plug 620 is kept in filling solution 622, and filling solution 622 may be contained in a tube, for example, a glass or plastic tube. In an example of the Ag/AgCl reference electrode, metal plug 620 may be silver (Ag), and filling solution 622 may be potassium chloride (KCl) solutions of various concentrations depending on the desired electrode potentials. For example, a KCl solution with concentrations ranging from 3 mol/kg (M) to saturation (>3.5 M) can reach a stable potential from +0.210 V to +0.197 V at 25° C. In an example of the Cu/Cu(II) reference electrode, metal plug 620 may be copper (Cu), and filling solution 622 may be copper (II) sulfate (Cu₂SO₄) solutions. For example, a saturated Cu₂SO₄ solution can reach a stable potential of +0.314 V at 25° C.

Tip 618 may be the part of reference electrode 604 in which a junction is provided in contact with both filling solution 622 and droplet 608 of fluid sample. Ionic conductivity can be achieved between filling solution 622 and droplet 608 via the junction so that the stable and known potential of reference electrode 604 can be applied to droplet 608. In some embodiments, tip 618 includes a frit 624 configured to form an electrical pathway (e.g., ionic conductivity) between filling solution 622 and droplet 608. Frit 624 may be made of a porous glass (e.g., Vycor glass). In some embodiments, other than a porous glass, frit 624 may be made of a material other than a porous glass and may be configured to prevent filling solution 622 from leaking into droplet 608, i.e., a leakless or leak-free frit. It is to be appreciated that in some embodiments, tip 618 may include a diaphragm, a membrane, or any other suitable structure that can allow ionic conductivity between filling solution 622 and droplet 608.

In some embodiments, fluid dispenser 606 is integrated with reference electrode 604 by at least partially surrounding tip 618 of reference electrode 604. Fluid dispenser 606 includes an inlet 626, a chamber 628, and an outlet 630. Fluid dispenser 606 is configured to receive a fluid sample from inlet 626 to chamber 628. The fluid sample may be a buffer solution containing capture reagents, target reagents, wash solution, or any other biological or chemical species. Fluid dispenser 606 is further configured to form droplet 608 through outlet 630. Chamber 628 may be the main part of fluid dispenser 606 that can hold the fluid sample before dispensing it onto DUT 610. Each of inlet 626 and outlet 630 may be one or more openings formed on or connect to a respective end of chamber 628. In some embodiments, outlet 630 through which droplet 608 is formed surrounds tip 618 of reference electrode 604. The above-described design can ensure that droplet 608 formed through outlet 630 of fluid dispenser 606 is in fluidic contact with tip 618 of reference electrode 604. As a result, the known potential determined by reference electrode 604 can also be associated with droplet 608.

In some embodiments, probe card 612 includes a printed circuit board (PCB) 632 with an opening in which apparatus 602 can be inserted. In some embodiments, the dimensions of PCB 632 may be 130 cm×115 cm×0.3 cm (length×width× thickness). Probe card 612 includes a ring 634 in the opening and configured to dock apparatus 602 at a desired position in probe card 612. Probe card 612 also includes contact elements, such as solders 636 and terminal pins 638 configured to provide an electrical path between an electronic test system, e.g., controller 106, and DUT 610 on device substrate 614. Probe card 612 also includes movement mechanisms (not shown) configured to move probe card 612 in a plane parallel to device substrate 614 as well as in a direction perpendicular to device substrate 614. As apparatus 602 integrating reference electrode 604 and fluid dispenser 606 is docked in probe card 612, probe card 612 can move apparatus 602 to the precise position above DUT 610 for delivering droplet 608 at a desired position. As described above, the fluidic contact between droplet 608 and tip 618 of reference electrode 604 can be simultaneously achieved by arranging fluid dispenser 606 at least partially surrounding tip 618 of reference electrode 604, according to some embodiments. Thus, even with a relatively small amount of fluid sample delivered from fluid dispenser 606, the fluid continuity between droplet 608 and reference electrode 604 can be achieved. For example, the volume of droplet 608 dispensed by apparatus 602 may be less than 100 nL such as between, for example, about 50 nL and about 100 nL.

Once droplet 608 is placed on DUT 610, the fluidic contact between droplet 608 and DUT 610 (e.g., any sensor described in the present disclosure or any other suitable sensors) is formed. As a result, a stable and known potential determined by reference electrode 604 can be maintained in droplet 608 during the testing of DUT 610.

Figure 7B:
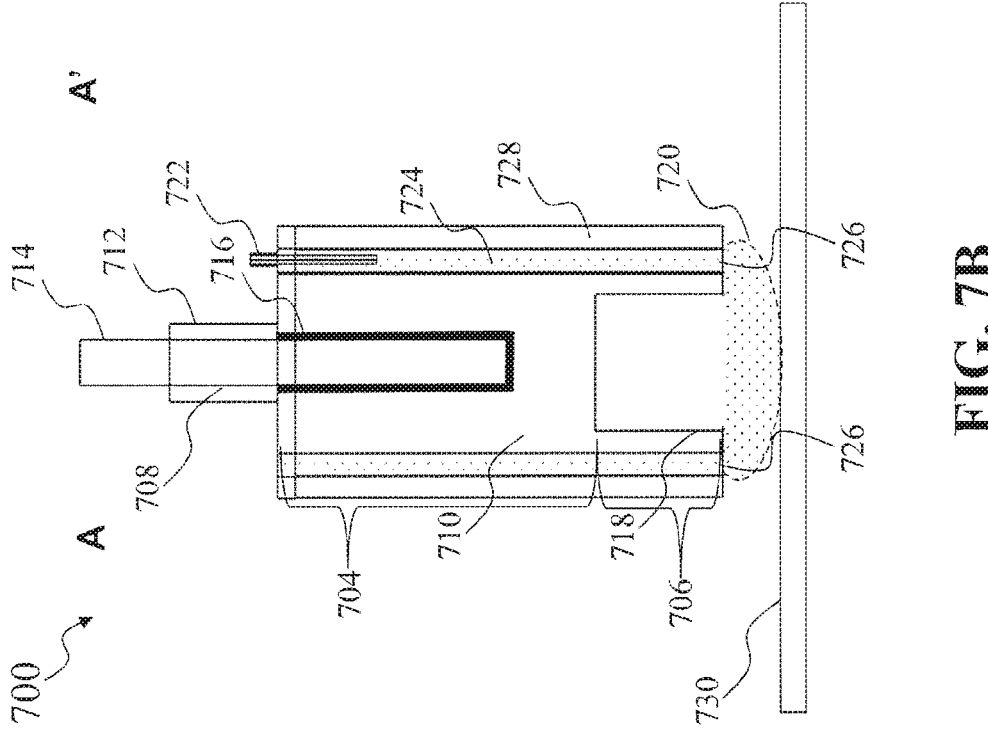
FIGS. 7A and 7B illustrate a perspective view and a cross-sectional view, respectively, of an exemplary apparatus including integrated reference electrode and fluid dispenser, according to some embodiments.
Figure 7A:
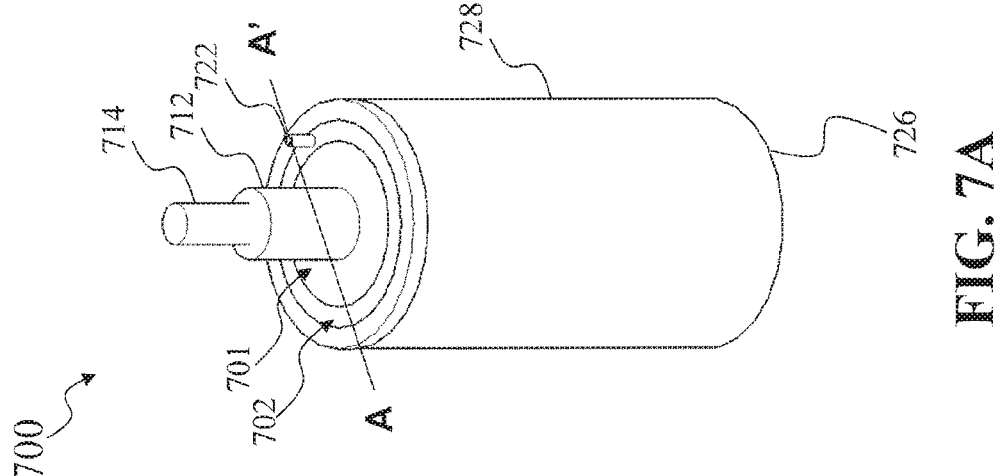

FIGS. 7A and 7B illustrate a perspective view and a cross-sectional view, respectively, of an exemplary apparatus 700 including an integrated reference electrode 701 and a fluid dispenser 702, according to some embodiments. In some embodiments, reference electrode 701 is an Ag/AgCl reference electrode including an electrode body 704 and an electrode tip 706. Electrode body 704 includes a silver plug 708 and a KCl electrolyte 710 as a filling solution. Silver plug 708 may be inserted and held through a cap 712 on top of a glass or plastic tube in which KCl electrolyte 710 is contained. An upper portion of silver plug 708 may act as or connects to an electrical terminal 714, which is the electrical input of reference electrode 701. A layer of silver chloride (AgCl) 716 is formed on a surface part of silver plug 708 immersed in KCl electrolyte 710 due to a reaction between silver plug 708 and KCl electrolyte 710.

Electrode tip 706 includes a frit 718 configured to form an electrical pathway (e.g., ionic conductivity) between KCl electrolyte 710 and a droplet 720 of fluid sample formed by fluid dispenser 702. In some embodiments, frit 718 is a leakless or leak-free frit that can prevent KCl electrolyte 710 from leaking into droplet 720 to avoid contamination to the fluid sample. Frit 718 may be inserted into an open end of a glass or plastic tube that contains KCl electrolyte 710. In some embodiments, the diameter of frit 718 may be about 1 mm, and the height of frit 718 may be about 3 mm.

In some embodiments, as shown in FIG. 7A, fluid dispenser 702 completely surrounds electrode tip 706 of reference electrode 701. Fluid dispenser 702 includes an inlet 722, a chamber 724, and an outlet 726. Inlet 722 may be a tube, or any fluid connector, which can connect chamber 724 to an external fluid sample source, e.g., a reservoir or a syringe pump. The fluid sample can thus be applied into chamber 724 via inlet 722. In some embodiments, the flow rate of fluid sample applied into chamber 724 is between about 5 uL/s and about 100 uL/s, such as 20 uL/s. Chamber 724 is formed between an enclosure 728 and an outer side surface of reference electrode 701. In some embodiments, the cross-section of chamber 724 (in the radial direction) has a ring-shape. In some embodiments, the diameter of enclosure 728 of fluid dispenser 702 is between about 2 mm and about 5 mm, such as 5 mm, and the height of enclosure 728 is between about 30 mm and about 100 mm, such as 65 mm. Outlet 726 is formed at or connects to an end of chamber 724. Droplet 720 is formed through outlet 726 by the gravity and/or external pressure applied to the fluid sample stored in chamber 724. In some embodiments, a mechanism (e.g., a door) may be included in fluid dispenser 702 to control an opening of outlet 726. The volume of droplet 720 can be controlled by fluid dispenser 702. In some embodiments, the volume of droplet 720 may be less than 100 nL, such as between about 50 nL and about 100 nL.

In operation, droplet 720 is formed through outlet 726 of fluid dispenser 702 and on a sensor 730. Droplet 720 is in fluidic contact with both electrode tip 706 (e.g., frit 718) of reference electrode 701 and sensor 730. Droplet 720 is also associated with the known reference potential determined by reference electrode 701 (e.g., +0.210 V at 25° C. when the molar concentration of KCl electrolyte 710 is 3 M). Sensor 730 may be any sensor described in the present disclosure. It is also to be appreciated that sensor 730 can be any other suitable sensors that are tested with a fluid sample having a stable reference potential. In other words, the applications of apparatus 700 are not limited to the sensors described in the present disclosure, but can be extended to any suitable sensors, such as but not limited to, amperometric sensors, potentiometric sensors, and voltammetric sensors.

FIGS. 8A-8D illustrate cross-sections of various exemplary apparatuses each including integrated reference electrode and fluid dispenser, according to some embodiments. As described above, fluid dispenser 606 is integrated with reference electrode 604 in apparatus 602 by at least partially surrounding tip 618 of reference electrode 604. It is to be appreciated that the meaning of "at least partially surrounding" can encompass different manners, such as the examples shown in FIGS. 8A-8B.

In FIG. 8A, the fluid dispenser completely surrounds tip 802 of the reference electrode. A cross-section of a chamber 804 of the fluid dispenser (in the radial direction) has a ring-shape. In some embodiments, the outlet of the fluid dispenser may have a single ring-shaped opening. In some embodiments, the outlet of the fluid dispenser may include a plurality of openings arranged along a circle at an end of chamber 804. In some embodiments, the cross-section of chamber 804 may vary at different elevations in the axial direction. In some embodiments, chamber 804 may only surround the reference electrode toward the bottom of the fluid dispenser. That is, the reference electrode may not extend toward the top of the fluid dispenser.

In FIG. 8B, the fluid dispenser surrounds tip 802 of the reference electrode. Different from the example in FIG. 8A, the cross-section of chamber 806 of the fluid dispenser (in the radial direction) is not limited to a ring-shape. In some embodiments, the outer surface of chamber 806 has an oval-shape, and the inner surface of chamber 806 has a circular-shape. In some embodiments, the outlet of the fluid dispenser may have a single opening in a planar shape that is the same as the cross-section of chamber 806. In some embodiments, the outlet of the fluid dispenser may include a plurality of openings surrounding tip 802 of the reference electrode at an end of chamber 806.

In FIG. 8C, the fluid dispenser completely surrounds tip 802 of the reference electrode. Different from the example in FIG. 8A, the cross-section of chamber 808 of the fluid dispenser (in the radial direction) is not limited to a ring-shape. In some embodiments, the outer surface of chamber 808 has a square-shape, and the inner surface of chamber 808 has a circular-shape. In some embodiments, the outlet of the fluid dispenser may have a single opening in a planar shape that is the same as the cross-section of chamber 808. In some embodiments, the outlet of the fluid dispenser may include a plurality of openings surrounding tip 802 of the reference electrode at an end of chamber 808.

Different from the examples in FIGS. 8A-8C, in FIG. 8D, the fluid dispenser partially surrounds tip 802 of the reference electrode. It is to be appreciated that although the cross-section of chamber 810 of the fluid dispenser (in the radial direction) is illustrated as a partial ring-shape, in some embodiments, the cross-sections of chambers of fluid dispensers that partially surround tip 802 of the reference electrode can be any shape. It is also to be appreciated that the examples shown in FIGS. 8A-8D are for illustrative purposes only and do not limit the design of apparatus 602. Apparatus 602 can integrate reference electrode 604 and fluid dispenser 606 in any suitable manner as long as fluid dispenser 606 partially surrounds tip 618 of reference electrode 604.

Figure 9:
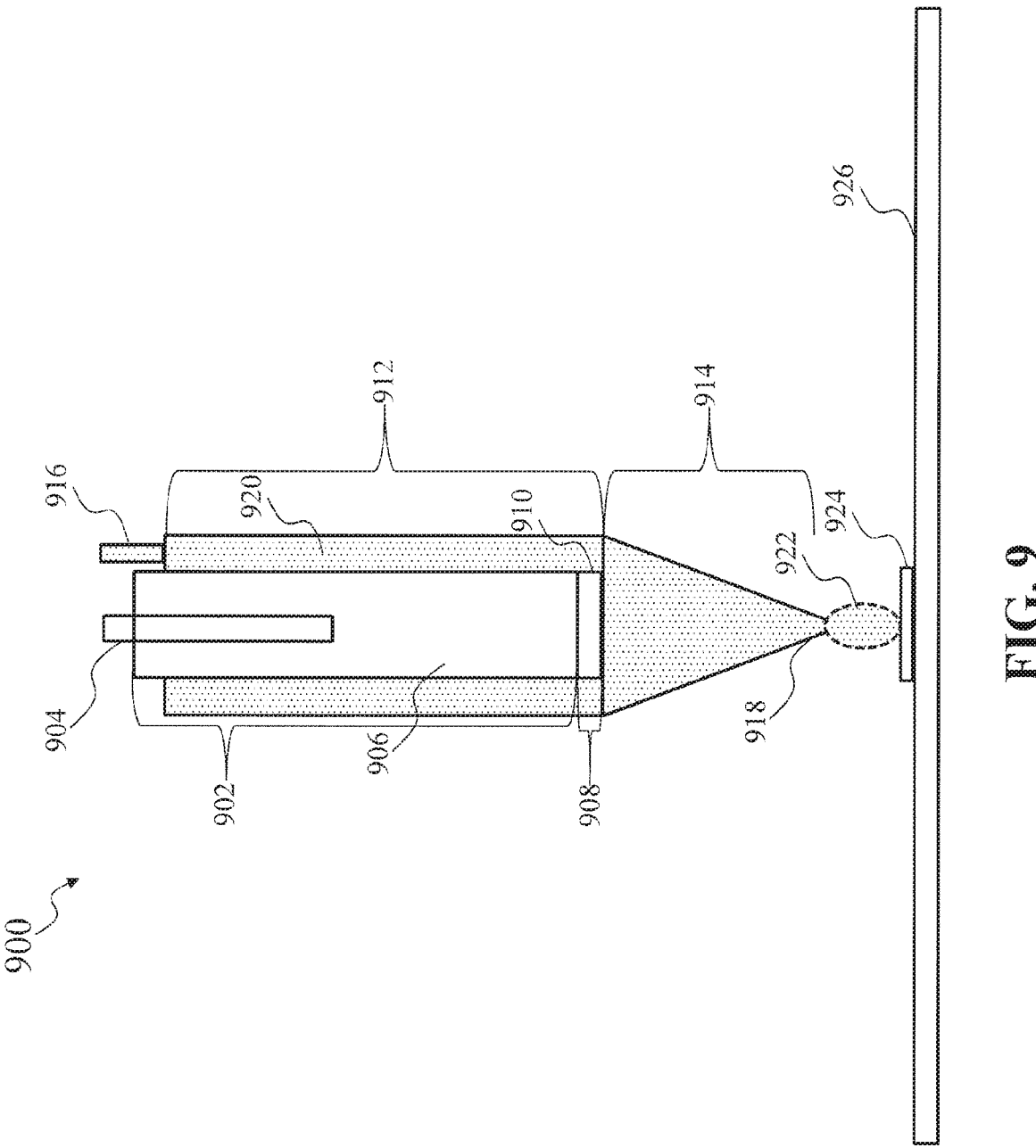
FIG. 9 illustrates another exemplary apparatus including an integrated reference electrode and a fluid dispenser for sensor characterization, according to some embodiments.

FIG. 9 illustrates another exemplary apparatus 900 including integrated reference electrode and fluid dispenser for sensor characterization, according to some embodiments. The reference electrode in apparatus 900 includes a body 902 having a metal plug 904 and a filling solution 906. The reference electrode also includes a tip 908 having a frit 910.

In the embodiments illustrated in FIGS. 6 and 7, the fluid dispenser is a cylinder with uniform diameters along the axial direction. The outlet of the fluid dispenser in the embodiments of FIGS. 6 and 7 is flush to the bottom surface of the tip of the reference electrode. In some embodiments, the fluid dispenser of apparatus 900 includes a dispenser body 912 and a dispenser tip 914. Dispenser body 912 is a cylinder, and dispenser tip 914 is substantially a cone. As shown in FIG. 9, an inlet 916 connects to or is formed at an end of dispenser body 912, and an outlet 918 is formed at a tip of dispenser tip 914. A first space between the enclosure of dispenser body 912 and the reference electrode is fluidically connected to a second space inside dispenser tip 914. The first and second spaces together form a chamber 920 of the fluid dispenser. Outlet 918 of the fluid dispenser is thus not flush to, but below the bottom surface of tip 908 of the reference electrode, according to some embodiments. As dispenser tip 914 becomes narrower towards outlet 918, a droplet 922 of the fluid sample, (with, for example, a smaller volume compared with the examples in FIGS. 6 and 7), can be dispensed by apparatus 900. Nevertheless, like the examples in FIGS. 6 and 7, in FIG. 9, the fluid dispenser surrounds tip 908 of the reference electrode to ensure that droplet 922 formed through outlet 918 is in fluidic contact with tip 908 of the reference electrode (e.g., via the fluid sample filled in the second space inside dispenser tip 914). In some embodiments, droplet 922 is also in fluidic contact with a sensor 924 on a substrate 926.

Referring to FIG. 10, an example method 1000 is presented. Method 1000 may be performed by system 600 to deliver a droplet of fluid sample to a surface of a sensor and apply a potential from a reference electrode to the droplet.

Other operations relating to fluid handling and electrical measurement not illustrated in method 1000 may be performed either before, between, or after the illustrated operations of method 1000. The various operations of method 1000 may be performed in a different order than described below.

At block 1002, an apparatus integrating a fluid dispenser and a reference electrode is held by a probe card. The fluid dispenser may be integrated with the reference electrode by at least partially surrounding the tip of the reference electrode. The integrated fluid dispenser and reference electrode may be docked in the PCB of the probe card by a ring in an opening at the PCB.

At block 1004, the probe card is moved so that the integrated fluid dispenser and reference electrode are moved together to a position above a sensor. The movement of the probe card, as well as the integrated fluid dispenser and reference electrode, may be in a plane parallel to the substrate forming the sensor and in a direction perpendicular to the substrate.

At block 1006, a potential is applied to the reference electrode. Depending on the type of the reference electrode (e.g., the metal plug and filling solution), a stable and known reference electrode potential can be reached at the body of the reference electrode.

At block 1008, a fluid sample is applied into a chamber of the fluid dispenser from an inlet of the fluid dispenser that partially surrounds the tip of the reference electrode. The fluid sample may be a buffer solution containing capture reagents, target reagents, wash solution, or any other biological or chemical species.

At block 1010, a droplet of the fluid sample is formed through an outlet of the fluid dispenser so that the droplet is in fluidic contact with both the tip of the reference electrode and the sensor and is associated with the potential applied to the reference electrode. The size and/or shape of the droplet may be determined by the design of the chamber and/or outlet of the fluid dispenser. The size and/or shape of the droplet may be also determined based on how in the fluid sample is pushed through the outlet such as, for example, the pressure, duration, interval, etc. The volume of the droplet may be less than about 100 nL, such as between about 50 nL and about 100 nL.

Further operations may be performed in order to provide complete fluid delivery for each stage of an assay. For example, following block 1010, another fluid sample may be applied into the chamber of the fluid dispenser from the inlet to replace the previous fluid sample in the chamber. Another droplet of the new fluid sample may be then formed through the outlet of the fluid dispenser. Due to the integration of the fluid dispenser and reference electrode, each time a new fluid sample is applied into the fluid dispenser and forms a new droplet in fluidic contact with the tip of the reference electrode, the reference electrode (e.g., the tip) is automatically cleaned by the new fluid sample without the need of a cleaning step using a washing solution. That is, self-cleaning of the reference electrode can be achieved by the integrated fluid dispenser and reference electrode.

Chemistry, Biology, and Interface

Figure 11:
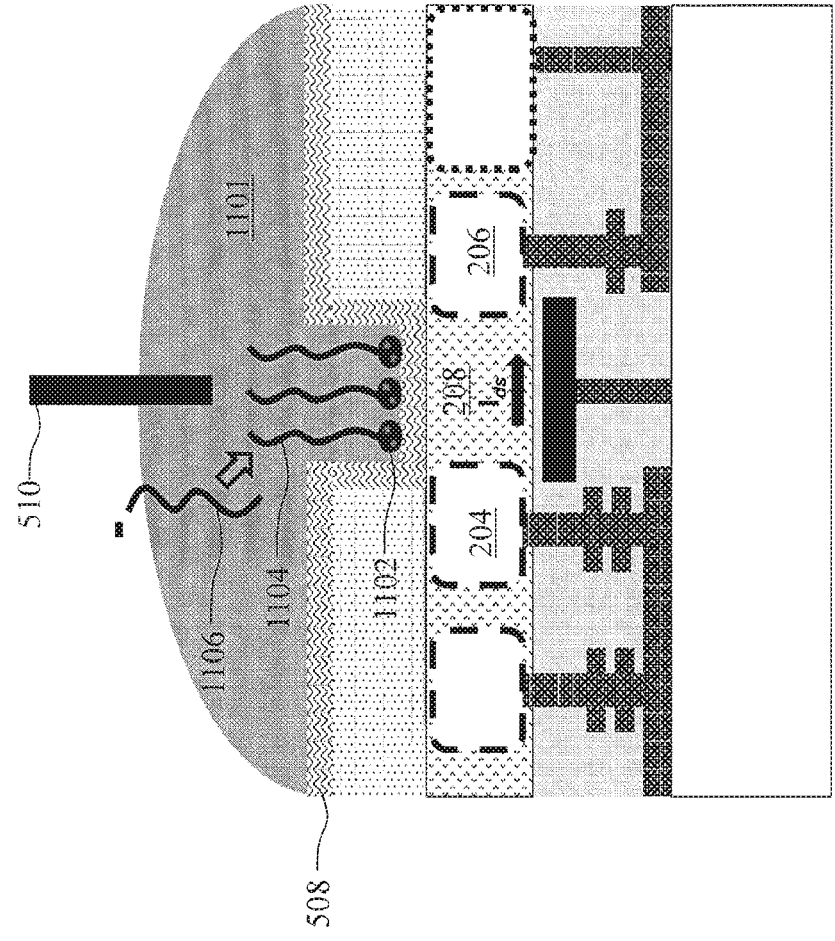
FIG. 11 is a cross-sectional view of an exemplary dual gate back-side sensing BioFET detecting DNA, according to some embodiments.

The apparatus, systems, and methods of the present disclosure can be used to deliver various fluids for the detection and/or monitoring of interactions between various entities. These interactions include biological and chemical reactions to detect target analytes in a test sample. As an example, reactions, including physical, chemical, biochemical, or biological transformations, can be monitored to detect generation of intermediates, byproducts, products, and combinations thereof. In addition, the apparatus, systems, and methods of the present disclosure can be used to detect these reactions in various assays as described herein, including, but not limited to, circulating tumor cell assays used in liquid biopsies and chelation assays to detect the presence of heavy metals and other environmental pollutants. Such assays and reactions can be monitored in a single format or in an array format to detect, e.g., multiple target analytes. Biological Sensing Embodiments with DGBSS FET Sensor Referring to FIG. 11, an example biosensing test is performed using the dual gate back-side sensing FET sensor described above in FIG. 5. A probe DNA 1104 (an example of a capture reagent) is bound to interface layer 508 via a linking molecule 1102. Linking molecule 1102 may have a reactive chemical group that binds to a portion of interface layer 508. An example of linking molecules include thiols. Linking molecules may also be formed via silanization of the surface of interface layer 508, or by exposing the surface of interface layer 508 to ammonia ($NH_3$) plasma, to form reactive $NH_2$ groups on the surface. The silanization process involves sequentially exposing the surface of interface layer 508 to different chemicals to build up covalently-bounded molecules on the surface of interface layer 508, as would be generally understood by a person skilled in the relevant art. Probe DNA 1104 represents single stranded DNA. The dual gate back-side sensing FET sensor illustrated in FIG. 11 is one FET within a sensor array that would exist on a chip, according to some embodiments.

Probe DNA 1104 may be immobilized on interface layer 508 prior to subjecting the FET sensor to a fluid sample 1101. Fluid sample 1101 may be delivered to the surface of the FET sensor using system 600. Fluid sample 1101 may include the matching single stranded DNA sequence 1106 that binds strongly to its matching probe DNA 1104. The binding of additional DNA increases the negative charge present on interface layer 508 and directly above channel region 208 of the FET sensor.

Figure 12B:
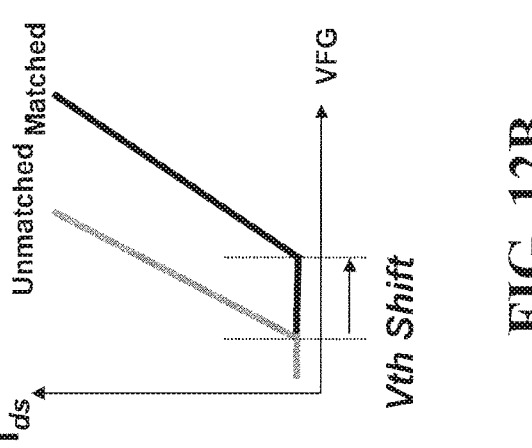
FIG. 12B illustrates a change in threshold voltage for the exemplary dual gate back-side sensing BioFET based on matched analyte binding, according to some embodiments.
Figure 12A:
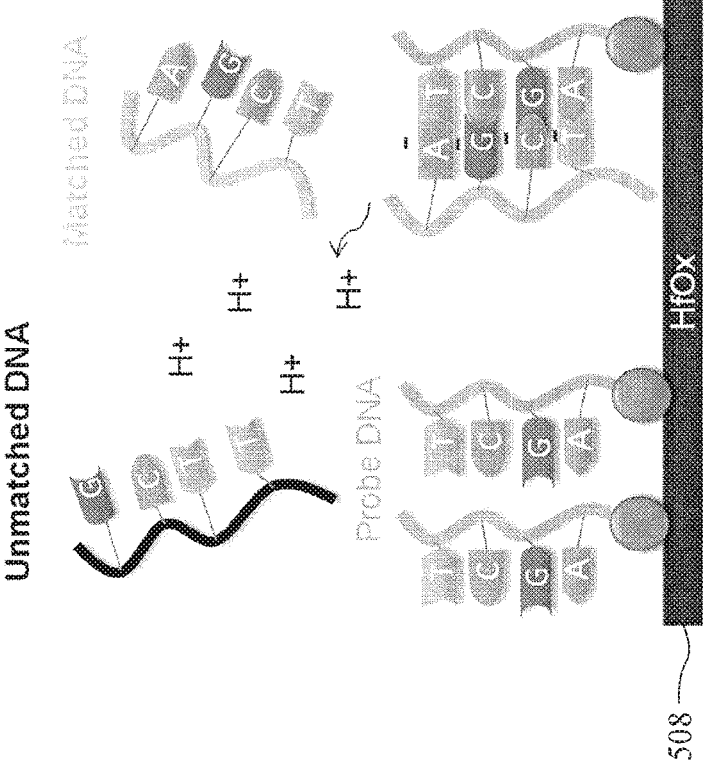
FIG. 12A illustrates the binding mechanism of DNA on a receptor surface, according to some embodiments.

The DNA binding is illustrated conceptually in FIG. 12A. Here, probe DNA having a nucleic acid sequence TCGA binds to its complementary matched strand having nucleic acid sequence AGCT. Any unmatched sequences will not hybridize with the probe DNA sequences. The binding of the matching DNA increases the negative charge built up at the interface of interface layer 508. In the example illustrated in FIG. 12A, interface layer 508 is hafnium oxide.

FIG. 12B illustrates a shift in the threshold voltage of the dual gate back-side sensing FET sensor when matching DNA is bound to the surface of interface layer 508. Briefly, voltage is applied to the reference electrode until the FET sensor "turns on" and current flows between drain region 206 and source region 204. The reference electrode may be represented by the reference electrodes as described in FIGS. 6-9. When more negative charge is present at interface layer 508 due to complementary DNA binding, a higher voltage is required to form the conductive inversion layer within channel region 208. Thus, according to some embodiments, a higher voltage may be applied to the reference electrode before the FET sensor conducts and $I_{ds}$ current flows. This difference in threshold voltage may be measured and used to determine the presence of the target matching DNA sequence and its concentration. It should be understood that a net positive accumulated charge at interface layer 508 would cause the threshold voltage to decrease rather than increase. Additionally, the change in threshold voltage will have the opposite sign for an n-channel FET as compared to a p-channel FET.

Figure 13:
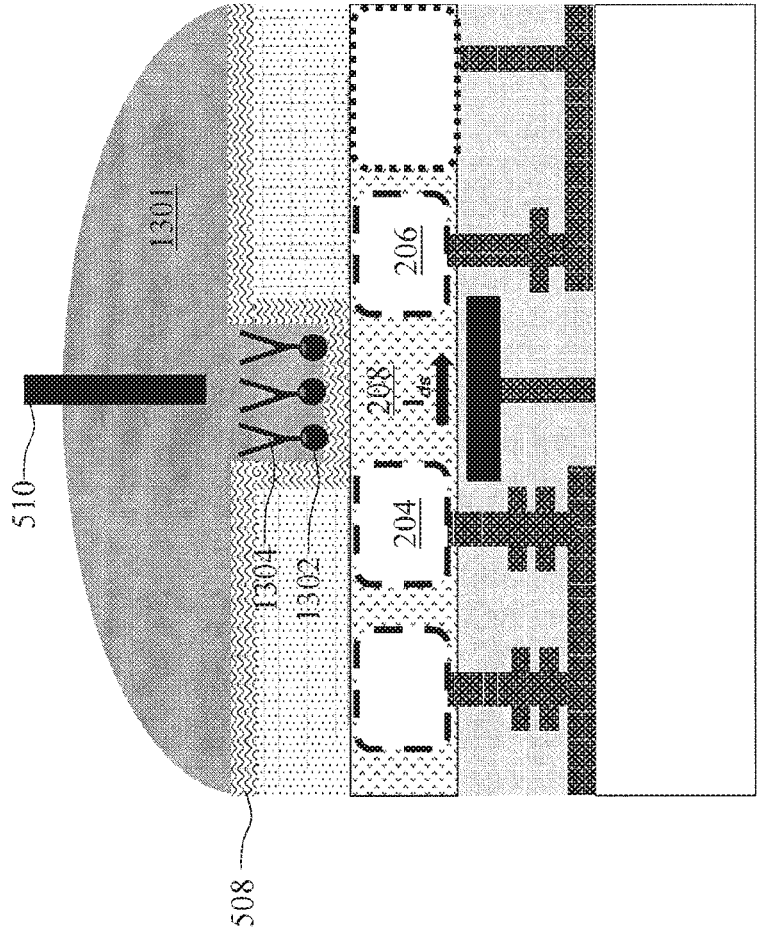
FIG. 13 is a cross-sectional view of an exemplary dual gate back-side sensing BioFET having antibodies immobilized on its sensing layer, according to some embodiments.

Referring to FIG. 13, another example biosensing test is performed using the dual gate back-side sensing FET sensor. Probe antibodies 1304 (another example of capture reagents) are bound to interface layer 508 via linking molecules 1302. Linking molecules 1302 may have a reactive chemical group that binds to a portion of interface layer 508. A fluid sample 1301 may be provided over probe antibodies 1304 to determine if the matching antigens are present within fluid sample 1301. Fluid sample 1301 may be delivered to the surface of the FET sensor using system 600.

Figure 14:
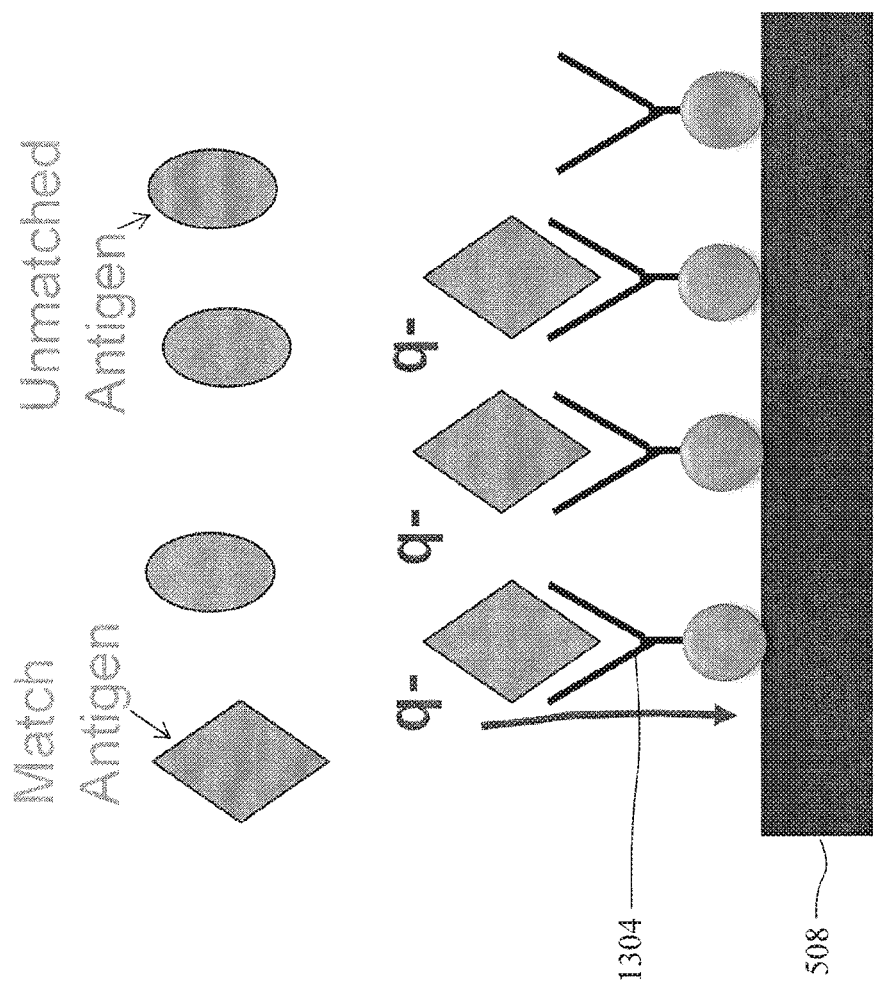
FIG. 14 illustrates the binding mechanism of antigens and antibodies on a receptor surface, according to some embodiments.

Referring to FIG. 14, the binding process of matching antigens to probe antibodies 1304 is illustrated. Here, matching antigens will bind to the immobilized probe antibodies while unmatched antigens will not bind. Similar to the DNA hybridization process described above, the matching antigens will change the accumulated charge present at interface layer 508. The shift in threshold voltage due to the accumulated charge from matching antibodies binding to the probe antibodies is measured in substantially the same way as already discussed above with reference to FIG. 12B.

Described herein are embodiments of an apparatus including integrated reference electrode and fluid dispenser. According to some embodiments, the apparatus includes a reference electrode and a fluid dispenser. The reference electrode includes a body and a tip. The fluid dispenser at least partially surrounds the tip of the reference electrode and includes an inlet, a chamber, and an outlet. The fluid dispenser is configured to receive a fluid sample from the inlet to the chamber and form a droplet of the fluid sample through the outlet so that the droplet is in fluidic contact with the tip of the reference electrode and associated with a known potential determined by the reference electrode.

According to some embodiments, a system includes a reference electrode, a fluid dispenser, and a probe card. The reference electrode includes a body and a tip. The fluid dispenser at least partially surrounds the tip of the reference electrode and includes an inlet, a chamber, and an outlet. The fluid dispenser is configured to receive a fluid sample from the inlet to the chamber and form a droplet of the fluid sample through the outlet so that the droplet is in fluidic contact with the tip of the reference electrode and associated with a known potential determined by the reference electrode. The probe card is configured to hold the fluid dispenser and reference electrode so that the fluid dispenser and reference electrode are moved together as the probe card moves.

According to some embodiments, the method includes applying a potential to a reference electrode including a body and a tip. The method also includes applying a fluid sample into a chamber of a fluid dispenser from an inlet of the fluid dispenser. The fluid dispenser at least partially surrounds the tip of the reference electrode. The method further includes forming a droplet of the fluid sample through an outlet of the fluid dispenser so that the droplet is in fluidic contact with the tip of the reference electrode and associated with the potential applied to the reference electrode.

It is to be appreciated that the Detailed Description section, and not the Abstract of the Disclosure section, is intended to be used to interpret the claims. The Abstract of the Disclosure section may set forth one or more but not all exemplary embodiments of the present disclosure as contemplated by the inventor(s), and thus, is not intended to limit the present disclosure and the subjoined claims in any way.

It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the subjoined claims and their equivalents.

What is claimed is:

1. An apparatus, comprising:
a reference electrode, comprising:
an electrode body,
a metal plug,
a filling solution, wherein the metal plug and the filling solution are disposed in the electrode body, and
a frit disposed in the electrode body, wherein sidewalls of the frit are in contact with the filling solution; and
a dispenser, comprising:
a chamber configured to hold a fluid sample,
an enclosure surrounding the chamber; and
an outlet configured to output a droplet of the fluid sample,
wherein the chamber surrounds the electrode body of the reference electrode,
wherein inner surfaces of the enclosure and outer surfaces of the electrode body are separated from each other by the chamber, and
wherein the droplet of the fluid sample is in fluidic contact with a tip of the reference electrode.

2. The apparatus of claim 1, wherein the reference electrode comprises a diaphragm or a membrane disposed within the tip of the reference electrode, and
wherein the diaphragm or the membrane provides conductivity between the filling solution and the droplet of the fluid sample.

3. The apparatus of claim 1, wherein an outer surface of the dispenser has a cross-sectional shape different from a cross-sectional shape of an inner surface of the dispenser.

4. The apparatus of claim 1, wherein an outer surface of the dispenser has an oval cross-sectional shape and an inner surface of the dispenser has a circular cross-sectional shape.

5. The apparatus of claim 1, wherein the outlet of the dispenser is coplanar with an outer surface of the tip of the reference electrode.

6. The apparatus of claim 1, wherein the dispenser comprises a control element configured to control an opening of an outlet of the dispenser.

7. The apparatus of claim 1, further comprising a cap disposed on a body of the reference electrode, wherein the cap is configured to support the metal plug within the body of the reference electrode.

8. The apparatus of claim 1, wherein the dispenser comprises an inlet tube coupled to the chamber.

9. The apparatus of claim 1, wherein top and bottom surfaces of the enclosure and the electrode body are coplanar.

10. An apparatus, comprising:
a reference electrode comprising an electrode body and an electrode tip, wherein the electrode body comprises a metal plug and a filling solution; and
a dispenser comprising a dispenser body and a dispenser tip,
wherein the dispenser body comprises a chamber surrounding the electrode body,
wherein sidewalls of the dispenser body and sidewalls of the electrode body are separated from each other by the chamber,
wherein an outlet of the electrode tip is coupled to an inlet of the dispenser tip and is wider than an outlet of the dispenser tip, and
wherein the dispenser tip is configured to output a droplet of a fluid in the chamber.

11. The apparatus of claim 10, wherein the fluid in the dispenser tip is in fluidic contact with the electrode tip.

12. The apparatus of claim 10, wherein the electrode tip comprises a frit and the frit is in fluidic contact with the fluid in the dispenser tip.

13. The apparatus of claim 10, wherein the dispenser body has a cross-sectional shape different from a cross-sectional shape of the electrode body.

14. The apparatus of claim 10, wherein the dispenser body has a cylindrical shape and the dispenser tip has a conical shape.

15. The apparatus of claim 10, wherein the metal plug extends out of the electrode body.

16. An apparatus, comprising:
a reference electrode, comprising:
an electrode tip; and
an electrode body, comprising:
a filling solution, and
a conductive plug disposed in the filling solution; and
a dispenser, comprising:
a dispenser body comprising a chamber surrounding the electrode body, wherein inner surfaces of the dispenser body and outer surfaces of the electrode body are separated from each other by the chamber, and wherein bottom surfaces of the dispenser body and the electrode body are coplanar; and
a dispenser tip disposed under the chamber, wherein an inlet of the dispenser tip is in contact with an outlet of the electrode tip.

17. The apparatus of claim 16, wherein the inlet of the dispenser tip is wider than the outlet of the electrode tip.

18. The apparatus of claim 16, wherein the reference electrode comprises a diaphragm or a membrane disposed in a tip of the reference electrode.

19. The apparatus of claim 16, wherein the chamber has a cross-sectional shape different from a cross-sectional shape of an outlet of the dispenser.

20. The apparatus of claim 16, wherein the dispenser has an oval cross-sectional shape and the electrode body has a circular cross-sectional shape.

* * * * *